United States Patent
Dix et al.

(10) Patent No.: US 11,098,127 B2
(45) Date of Patent: *Aug. 24, 2021

(54) STABILIZED FORMULATIONS CONTAINING ANTI-INTERLEUKIN-6 RECEPTOR (IL-6R) ANTIBODIES

(71) Applicant: Regeneron Pharmaceuticals, Inc., Tarrytown, NY (US)

(72) Inventors: Daniel B. Dix, LaGrangeville, NY (US); Kenneth S. Graham, Pleasant Valley, NY (US); Douglas Kamen, Poughquag, NY (US); Scott M. Walsh, Tarrytown, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/100,020

(22) Filed: Aug. 9, 2018

(65) Prior Publication Data

US 2019/0002574 A1    Jan. 3, 2019

Related U.S. Application Data

(63) Continuation of application No. 14/861,565, filed on Sep. 22, 2015, now Pat. No. 10,072,086, which is a continuation of application No. 12/986,223, filed on Jan. 7, 2011, now Pat. No. 9,173,880.

(60) Provisional application No. 61/293,227, filed on Jan. 8, 2010.

(51) Int. Cl.

| | |
|---|---|
| A61K 39/395 | (2006.01) |
| C07K 16/28 | (2006.01) |
| A61K 9/00 | (2006.01) |
| A61K 31/485 | (2006.01) |
| A61K 47/18 | (2017.01) |
| A61K 47/26 | (2006.01) |
| C07K 16/24 | (2006.01) |
| A61J 1/06 | (2006.01) |
| A61K 47/22 | (2006.01) |
| A61K 39/00 | (2006.01) |

(52) U.S. Cl.
CPC ........... *C07K 16/2866* (2013.01); *A61J 1/065* (2013.01); *A61K 9/0019* (2013.01); *A61K 31/485* (2013.01); *A61K 39/3955* (2013.01); *A61K 47/183* (2013.01); *A61K 47/22* (2013.01); *A61K 47/26* (2013.01); *C07K 16/248* (2013.01); *A61K 2039/505* (2013.01); *C07K 2317/21* (2013.01); *C07K 2317/515* (2013.01); *C07K 2317/94* (2013.01)

(58) Field of Classification Search
None
See application file for complete search history.

(56) References Cited

U.S. PATENT DOCUMENTS

| | | |
|---|---|---|
| 4,997,423 A | 3/1991 | Okuda et al. |
| 5,016,784 A | 5/1991 | Batson |
| 5,480,796 A | 1/1996 | Kishimoto |
| 5,605,690 A | 2/1997 | Jacobs et al. |
| 5,670,373 A | 9/1997 | Kishimoto |
| 5,723,120 A | 3/1998 | Brakenhoff et al. |
| 5,795,965 A | 8/1998 | Tsuchiya et al. |
| 5,817,790 A | 10/1998 | Tsuchiya et al. |
| 5,888,510 A | 3/1999 | Kishimoto et al. |
| 5,888,511 A | 3/1999 | Skurkovich et al. |
| 5,908,686 A | 6/1999 | Sudo et al. |
| 6,046,223 A | 4/2000 | Sponsel et al. |
| 6,086,874 A | 7/2000 | Yoshida et al. |
| 6,261,560 B1 | 7/2001 | Tsujnaka et al. |
| 6,286,699 B1 | 9/2001 | Sudo |
| 6,410,691 B1 | 6/2002 | Kishimoto |
| 6,629,949 B1 | 10/2003 | Douglas |
| 6,632,927 B2 | 10/2003 | Adair et al. |
| 6,645,635 B2 | 11/2003 | Murakai |
| 6,659,982 B2 | 12/2003 | Douglas et al. |
| 6,670,373 B1 | 12/2003 | Bonjouklian et al. |
| 6,692,742 B1 | 2/2004 | Nakamura et al. |
| 6,723,319 B1 | 4/2004 | Ito et al. |
| 7,226,554 B2 | 6/2007 | Sudo et al. |
| 7,320,792 B2 | 1/2008 | Ito et al. |
| 7,479,543 B2 | 1/2009 | Tsuchiya et al. |
| 7,582,298 B2 | 9/2009 | Stevens et al. |
| 8,043,617 B2 | 10/2011 | Stevens et al. |
| 8,080,248 B2 | 12/2011 | Radin et al. |
| 8,183,014 B2 | 5/2012 | Stevens et al. |
| 8,192,741 B2 | 6/2012 | Radin et al. |
| 8,568,721 B2 | 10/2013 | Radin et al. |
| 8,895,521 B2 | 11/2014 | Klinman et al. |

(Continued)

FOREIGN PATENT DOCUMENTS

| | | |
|---|---|---|
| EA | 014226 B1 | 10/2010 |
| EA | 014298 B1 | 10/2010 |
| EP | 0 628 639 A1 | 12/1994 |
| EP | 409607 B1 | 10/1996 |
| EP | 783893 A1 | 7/1997 |

(Continued)

OTHER PUBLICATIONS

Daugherty et al., "Formulation and delivery issues for monoclonal antibody therapeutics," *Adv. Drug Delivery Reviews*, 58:686-706, (2006).

(Continued)

*Primary Examiner* — Yunsoo Kim
(74) *Attorney, Agent, or Firm* — Schwabe, Williamson & Wyatt PC; Christopher Westberg

(57) ABSTRACT

The present invention provides pharmaceutical formulations comprising a human antibody that specifically binds to human interleukin-6 receptor (hIL-6R). The formulations may contain, in addition to an anti-hIL-6R antibody, at least one amino acid, at least one sugar, and/or at least one non-ionic surfactant. The pharmaceutical formulations of the present invention exhibit a substantial degree of antibody stability after storage for several months.

27 Claims, 4 Drawing Sheets

Specification includes a Sequence Listing.

(56) References Cited

U.S. PATENT DOCUMENTS

| | | |
|---|---|---|
| 9,139,646 B2 | 9/2015 | Solinger et al. |
| 9,173,880 B2 | 11/2015 | Dix et al. |
| 9,308,256 B2 | 4/2016 | Radin et al. |
| 9,884,916 B2 | 2/2018 | Stevens et al. |
| 9,943,594 B2 | 4/2018 | Jasson et al. |
| 1,007,208 A1 | 9/2018 | Dix et al. |
| 2002/0187150 A1 | 12/2002 | Mihara et al. |
| 2003/0092606 A1 | 5/2003 | L'Italien et al. |
| 2003/0113316 A1 | 6/2003 | Kaisheva et al. |
| 2003/0190316 A1 | 10/2003 | Kakuta et al. |
| 2004/0071706 A1 | 4/2004 | Ito et al. |
| 2004/0115197 A1 | 6/2004 | Yoshizaki et al. |
| 2004/0197324 A1 | 10/2004 | Liu et al. |
| 2004/0202658 A1 | 10/2004 | Benyunes |
| 2004/0219156 A1 | 11/2004 | Goldenberg et al. |
| 2005/0142635 A1 | 6/2005 | Tsuchiya et al. |
| 2005/0238644 A1 | 10/2005 | Mihara et al. |
| 2006/0078531 A1 | 4/2006 | Sota |
| 2006/0078532 A1 | 4/2006 | Omoigui |
| 2006/0078533 A1 | 4/2006 | Omoigui |
| 2006/0177436 A1 | 8/2006 | Ghilardi et al. |
| 2006/0251653 A1 | 11/2006 | Okuda et al. |
| 2006/0275294 A1 | 12/2006 | Omoigui |
| 2006/0292147 A1 | 12/2006 | Yoshizaki et al. |
| 2007/0036785 A1 | 2/2007 | Kishimoto |
| 2007/0036788 A1 | 2/2007 | Sheriff et al. |
| 2007/0098714 A1 | 5/2007 | Nishimoto et al. |
| 2007/0148169 A1 | 6/2007 | Yoshizaki et al. |
| 2007/0280945 A1 | 12/2007 | Stevens et al. |
| 2008/0124325 A1 | 5/2008 | Ito et al. |
| 2008/0131374 A1 | 6/2008 | Medich et al. |
| 2008/0145367 A1 | 6/2008 | Bove et al. |
| 2008/0269467 A1 | 10/2008 | Allan et al. |
| 2009/0082288 A1 | 3/2009 | Klinman et al. |
| 2010/0316627 A1 | 12/2010 | Stevens et al. |
| 2010/0316636 A1 | 12/2010 | Radin et al. |
| 2011/0098450 A1 | 4/2011 | Igawa et al. |
| 2011/0171241 A1 | 7/2011 | Dix et al. |
| 2011/0245473 A1 | 10/2011 | Igawa et al. |
| 2012/0003697 A1 | 1/2012 | Stevens et al. |
| 2012/0171123 A1 | 7/2012 | Medich et al. |
| 2012/0258098 A1 | 10/2012 | Radin et al. |
| 2013/0149310 A1 | 6/2013 | Jasson et al. |
| 2014/0255390 A1 | 9/2014 | Radin et al. |
| 2014/0302053 A1 | 10/2014 | Huang et al. |
| 2015/0050277 A1 | 2/2015 | Peters et al. |
| 2016/0002341 A1 | 1/2016 | Dix et al. |
| 2016/0229916 A1 | 8/2016 | Stevens et al. |
| 2016/0280782 A1 | 9/2016 | Huang et al. |
| 2017/0252434 A1 | 9/2017 | Joseph et al. |
| 2018/0296670 A1 | 10/2018 | Jasson et al. |
| 2019/0002574 A1 | 1/2019 | Dix et al. |

FOREIGN PATENT DOCUMENTS

| | | |
|---|---|---|
| EP | 800829 A1 | 10/1997 |
| EP | 811384 A1 | 12/1997 |
| EP | 923941 A2 | 6/1999 |
| EP | 1 004 315 A1 | 5/2000 |
| EP | 1074268 A1 | 2/2001 |
| EP | 1 108 435 A1 | 6/2001 |
| EP | 1314437 A1 | 5/2003 |
| EP | 1 327 681 A1 | 7/2003 |
| EP | 1475100 A1 | 11/2004 |
| EP | 1475101 A1 | 11/2004 |
| EP | 0 413 908 B2 | 8/2005 |
| EP | 1810980 A1 | 7/2007 |
| EP | 1 334 731 B1 | 2/2008 |
| EP | 2238985 A1 | 10/2010 |
| FR | 2694767 A1 | 2/1994 |
| JP | 2009-539349 A | 11/2009 |
| RU | H32358762 C2 | 6/2009 |
| WO | 1992/016553 A1 | 10/1992 |
| WO | 1992/019759 A1 | 11/1992 |
| WO | 1994/006476 A1 | 3/1994 |
| WO | 1995/009873 A1 | 4/1995 |
| WO | 1996/011020 A1 | 4/1996 |
| WO | 2002/100330 A2 | 12/2002 |
| WO | 03/009817 A2 | 2/2003 |
| WO | 04/039826 A1 | 5/2004 |
| WO | 04/091658 A1 | 10/2004 |
| WO | 2004/096273 A1 | 11/2004 |
| WO | 05/016280 A2 | 2/2005 |
| WO | 05/028514 A1 | 3/2005 |
| WO | 05/058365 A1 | 6/2005 |
| WO | 2006/033702 A2 | 3/2006 |
| WO | 07/062040 A1 | 5/2007 |
| WO | 2007/070750 A1 | 6/2007 |
| WO | 07/143168 A2 | 12/2007 |
| WO | 07/147001 A2 | 12/2007 |
| WO | 08/020079 A1 | 2/2008 |
| WO | 2007/143168 A3 | 4/2008 |
| WO | 08/049897 A1 | 5/2008 |
| WO | 2008/145142 A1 | 12/2008 |
| WO | 09/095489 A2 | 8/2009 |
| WO | 2009/109584 A1 | 9/2009 |
| WO | 09/125825 A1 | 10/2009 |
| WO | 2010/035769 A1 | 4/2010 |
| WO | 2010/106812 A1 | 9/2010 |
| WO | 2010/149771 A1 | 12/2010 |
| WO | 11/085158 A2 | 7/2011 |
| WO | 2013/053751 A1 | 4/2013 |
| WO | 2015/077582 A1 | 5/2015 |
| WO | 2015/148790 A1 | 10/2015 |
| WO | 2016/044343 A1 | 3/2016 |
| WO | 2017/079443 A1 | 5/2017 |
| WO | 2017/155990 A1 | 9/2017 |

OTHER PUBLICATIONS

Meehan et al., "A microinfusor device for the delivery of therapeutic levels of peptides and macromolecules," *Journal of Controlled Release*, 46:107-116 (1996).

Patro et al., "Protein formulation and fill-finish operations," Biotechnol Annu Rev, 8:55-84, (2002). Abstract only.

PCT International Preliminary Report of Patentability for application PCT/US2011/020457 dated Jul. 10, 2012.

PCT International Search Report for application PCT/US2011/020457 dated Feb. 7, 2011.

PCT Written Opinion of the International Searching Authority for application PCT/US2011/020457 dated Feb. 7, 2011.

Reddy et al., "Elimination of Fc Receptor-Dependent Effector Functions of a Modified IgG4 Monoclonal Antibody to Human CD4," *Journal of Immunology*, 164:1925-1933 (2000).

Shields et al., "Lack of Fucose on Human IgG1 N-Linked Oligosaccharide Improves Binding to Human Fc gamma RIII and Antibody-dependent Cellular Toxicity," *Journal of Biological Chemistry*, 277(30):26733-26740 (2002).

U.S. Appl. No. 12/986,223, Final Office Action dated Apr. 27, 2012.

U.S. Appl. No. 12/986,223, Non-Final Office Action dated Feb. 14, 2012.

U.S. Appl. No. 12/986,223, Non-Final Office Action dated Feb. 9, 2015.

U.S. Appl. No. 12/986,223, Non-Final Office Action dated Nov. 15, 2013.

U.S. Appl. No. 12/986,223, Notice of Allowance dated Jun. 22, 2015.

U.S. Appl. No. 12/986,223, Requirement for Restriction/Election dated Dec. 30, 2011.

U.S. Appl. No. 14/861,565, Final Office Action dated Jan. 17, 2018.

U.S. Appl. No. 14/861,565, Non-Final Office Action dated Aug. 4, 2017.

U.S. Appl. No. 14/861,565, Notice of Allowance dated May 10, 2018.

U.S. Appl. No. 12/986,223, Final Office Action dated May 14, 2014.

Wang et al., "Minireview: Antibody Structure, Instability, and Formulation," Journal of Pharmaceutical Sciences, 96(1):1-26, (2007).

Wang, "Instability, stabilization, and formulation of liquid protein pharmaceuticals," *Int'l J. Pharmaceutics*, 185(2):129-188, (1999).

U.S. Appl. No. 61/293,227, filed Jan. 8, 2010, Expired.

(56) References Cited

OTHER PUBLICATIONS (2011) International Nonproprietary Names (INN) for Pharmaceutical Substances, World Health Organization, 53 Pages.
(Apr. 13, 2015) Phase II Study to Analyze Sarilumab in Non-Infectious Uveitis, NCT01900431 on Apr. 13, 2015, ClinicalTrials.gov Archive, URL: https://clinicaltrials.gov/archive/NCT01900431.
(Oct. 29, 2010) Study of the Safety, Tolerability, and Bioactivity of Tocilizumab on Patients with Non-infectious UVEITIS: The STOP-UVEITIS Study (STOP-Uveitis), Available at: https://clinicaltrials.gov/ct2/show/NCT01717170.
(Oct. 30, 2012) Study of the Safety, Tolerability, and Bioactivity of Tocilizumab on Patients with Non-infectious UVEITIS, The STOP-UVEITIS Study, ClinicalTrials.gov Archive.
Adan, et al. (Jul. 27, 2013) "Tocilizumab Treatment for Refractory Uveitis-Related Cystoid Macular Edema", Graefes Archive for Clinical and Experimental Ophthalmology, vol. 251, No. 11, pp. 2627-2632.
Amit, et al. (Aug. 15, 1986) "Three-Dimensional Structure of An Antigen-Antibody Complex At 2.8 A Resolution", Science, vol. 233, No. 4765, pp. 747-753.
Advisory Action received for U.S. Appl. No. 13/648,521, dated Jul. 19, 2016, 3 Pages.
Aletaha, et al. (Sep. 2010) "Rheumatoid Arthritis Classification Criteria: An American College of Rheumatology/European League Against Rheumatism Collaborative Initiative", Arthritis and Rheumatology, vol. 62, No. 9, pp. 2569-2581.
An, et al. (Jan. 2010) "The Addition of Tocilizumab to DMARD Therapy for Rheumatoid Arthritis: A Meta-Analysis of Randomized Controlled Trials", European Journal of Clinical Pharmacology, vol. 66, No. 1, pp. 49-59.
Arevalo, J Fernando, (Nov. 25, 2014) "Tocilizumab Shows Promise for Refractory Uveitis-Related Macular Edema", URL: https://www.aao.org/editors-choice/tocilizumab-shows-promise-refractory-uveitisrelate.
Barry, et al. (Sep. 1, 2014) "Pharmacotherapy for Uveitis: Current Management and Emerging Therapy", Clinical Ophthalmology, vol. 8, pp. 1891-1911.
Bresnick, George H. (Jul. 1986) "Diabetic Macular Edema. A Review.", Ophthalmology, vol. 93, Issue 7, pp. 989-997.
Burmester, et al. (Jan. 2014) "A Randomised, Double-Blind, Parallel-Group Study of the Safety and Efficacy of Subcutaneous Tocilizumab Versus Intravenous Tocilizumab in Combination with Traditional Disease-Modifying Antirheumatic Drugs in Patients with Moderate to Severe Rheumatoid Arth", Annals of the Rheumatic Diseases, vol. 73, No. 1, pp. 69-74.
Burmester, et al. (May 2017) "Efficacy and Safety of Sarilumab Monotherapy Versus Adalimumab Monotherapy for The Treatment of Patients with Active Rheumatoid Arthritis (MONARCH): A Randomised, Double-Blind, Parallel-Group Phase III Trial", Annals of the Rheumatic Diseases, vol. 76, No. 5, pp. 840-847.
Cao, et al. (Jun. 2013) "Pharmacological Blockade of Interleukin 6 Receptor (IL-6R) Inhibits the Development of Ocular Inflammation in the Murine Model of Experimental Autoimmune Uveitis (EAU)", Investigative Ophthalmology & Visual Science, vol. 54, Issued 15, 5193 Page.
Chester (Jul. 24, 2017) E-mail: "<External> CAS Registry No. RN1189541-98-7".
Chichasova, et al. (2010) "Treatment of Rheumatoid Arthritis: Tactical Issues in the Practice of the Clinician", The Attending Physician, No. 7/10.
Davis, et al. (Nov. 2010) "Scale for Photographic Grading of Vitreous Haze in Uveitis", American Journal of Ophthalmology, vol. 150, No. 5, pp. 637-641. Pharmacology of TNF blockade.
Durrani, et al. (Sep. 2004) "Degree, Duration, And Causes of Visual Loss in Uveitis", British Journal of Ophthalmology, vol. 88, No. 9, pp. 1159-1162.
Emery, et al. (Nov. 2008) "IL-6 Receptor Inhibition with Tocilizumab Improves Treatment Outcomes in Patients with Rheumatoid Arthritis Refractory to Anti-Tumour Necrosis Factor Biologicals: Results From a 24-Week Multicentre Randomised Placebo-Controlled Trial", Annals of the Rheumatic Diseases, vol. 67, No. 11, pp. 1516-1523.

Final Office Action received for U.S. Appl. No. 13/648,521, dated Mar. 10, 2014, 9 Pages.
Final Office Action received for U.S. Appl. No. 13/648,521, dated Feb. 11, 2016, 12 Pages.
Fleischmann, et al. (Oct. 2014) "Comparable Efficacy with Sarilumab Plus Methotrexate in Biologic-Experienced and Biologic-Naïve Patients with Moderate-to-Severe Rheumatoid Arthritis from a Phase 3, Randomized, Double-Blind, Placebo-Controlled, International Study", Arthritis & Rheumatology, vol. 66, No. S10, pp. S1232.
Gandek, et al. (Summer 2004) "Psychometric Evaluation of the SF-36® Health Survey in Medicare Managed Care", Health Care Financing Review, vol. 25, No. 4, pp. 5-25.
Genentech, et al. (2014) "ACTEMRA Subcutaneous Dosing & Administration Pocket Guide", pp. 1-40.
Genovese, et al. (Jun. 2015) "Sarilumab Plus Methotrexate in Patients with Active Rheumatoid Arthritis and Inadequate Response to Methotrexate: Results of a Phase III Study", Arthritis & Rheumatology, vol. 67, No. 6, pp. 1424-1437.
Gordon, et al. (Jul. 1998) "pANCA Antibodies in Patients with Anterior Uveitis: Identification of A Marker Antibody Usually Associated with Ulcerative Colitis", Journal of Clinical Immunology, vol. 18, No. 4, pp. 264-271.
Haq (Jul. 30, 2019) "Scleroderma Study Conference", English Translation, Retrieved from URL: <<http://derma.w3.kanazawa-u.ac.jp/SSc/pamphret/HAQ.html>>, 6 Pages (4 Pages of English Translation & 2 Pages of Official Copy).
Hennigan, et al. (Aug. 2008) "Interleukin-6 Inhibitors in the Treatment of Rheumatoid Arthritis", Therapeutics and clinical risk management, vol. 4, No. 4, pp. 767-775.
Hirata, et al. (Nov. 1, 1989) "Characterization of IL-6 Receptor Expression by Monoclonal and Polyclonal Antibodies", The Journal of Immunology, vol. 143, No. 9, pp. 2900-2906.
Huizinga, et al. (Sep. 2014) "Sarilumab, A Fully Human Monoclonal Antibody Against IL-6Rα in Patients with Rheumatoid Arthritis and an Inadequate Response to Methotrexate: Efficacy and Safety Results from the randomised SARIL-RA-MOBILITY Part A Trial", Annals of the Rheumatic Diseases, vol. 73, No. 9, pp. 1626-1629.
International Search Report and Written Opinion received for PCT Patent Application No. PCT/EP2012/070052, dated Jan. 10, 2013, 10 Pages.
International Search Report and Written Opinion received for PCT Patent Application No. PCT/US2012/070052, dated Mar. 18, 2013, 7 Pages.
International Search Report and Written Opinion received for PCT Patent Application No. PCT/US2014/066856, dated Apr. 2, 2015, 11 Pages.
International Search Report and Written Opinion received for PCT Patent Application No. PCT/US2015/050291, dated Dec. 1, 2015, 12 Pages.
International Search Report and Written Opinion received for PCT Patent Application No. PCT/US2016/060344, dated Mar. 13, 2017, 13 pages.
International Search Report and Written Opinion received for PCT Patent Application No. PCT/US2017/021149, dated Jul. 18, 2017, 14 Pages.
Kawashima, et al. (Apr. 6, 2007) "Soluble IL-6 Receptor in Vitreous Fluid of Patients with Proliferative Diabetic Retinopathy", Japanese Journal of Ophthalmology, vol. 51, No. 2, pp. 100-104.
Kishimoto, et al. (2003) "Interleukin-6 (IL-6)", The Cytokine Handbook. Ed.: Thomson. Academic Press. London, United Kingdom, vol. 12, pp. 281-304.
Kivitz, et al. (Nov. 2014) "Subcutaneous Tocilizumab Versus Placebo in Combination with Disease-Modifying Antirheumatic Drugs in Patients with Rheumatoid Arthritis", Rheumatoid Arthritis, vol. 66, Issue 11, pp. 1653-1661.
Langer, Robert (Sep. 28, 1990) "New Methods of Drug Delivery", Science, vol. 249, Issue 4976, pp. 1527-1533.
Lederman, et al. (Nov. 1991) "Single Amino Acid Substitution in a Common African Allele of The CD4 Molecule Ablates Binding of The Monoclonal Antibody, OKT4", Molecular Immunology, vol. 28, No. 11, pp. 1171-1181.

(56) References Cited

OTHER PUBLICATIONS

Li, et al. (May 2004) "Temporal Associations Between Interleukin 22 and the Extracellular Domains Of IL-22R and IL-1 OR2", International Immunology, vol. 4, No. 5, pp. 693-708.
Lin, Phoebe (Sep. 1, 2015) "Targeting Interleukin-6 For Noninfectious Uveitis", Clinical Ophthalmology, vol. 9, pp. 1697-1702.
Lipsky, Peter E. (2006) "Interleukin-6 and Rheumatic Diseases", Arthritis Research & Therapy, vol. 8, Suppl 2, S4, pp. 1-5.
McGovern, Timothy J. (Oct. 19, 2016) "Center for Drug Evaluation and Research", Application No. 761037Orig1s000, pp. 01-278.
Merida, et al. (Aug. 11, 2015) "New Immunosuppressive Therapies in Uveitis Treatment", International Journal of Molecular Sciences, vol. 16, No. 8, pp. 18778-18795.
Mesquida, et al. (Sep. 6, 2014) "Long-Term Effects of Tocilizumab Therapy for Refractory Uveitis-Related Macular Edema", Ophthalmology, vol. 121, No. 12, pp. 2380-2386.
Mihara, et al. (Nov. 2005) "Tocilizumab Inhibits Signal Transduction Mediated by Both mIL-6R and sIL-6R, But Not by The Receptors Of Other Members Of IL-6 Cytokine Family", International Immunopharmacology, vol. 5, No. 12, pp. 1731-1740.
Nguyen, et al. (Jun. 2015) "The SATURN Study (SARIL-NIU): Sarilumab for the Treatment of Posterior Segment Non-Infectious Uveitis (NIU)", Investigative Ophthalmology & Visual Science, vol. 56, No. 7, 3116 pages.
Nicassio, et al. (Jan. 2012) "The Contribution of Pain and Depression to Self-Reported Sleep Disturbance in Patients with Rheumatoid Arthritis", Pain, vol. 153, No. 1, pp. 107-112.
"Nihon Naika Gakkai zasshi", Japan Internal Medical Association Magazine, vol. 101, No. 10, pp. 2893-2898.
Nishimoto, et al. (Nov. 1, 2008) "Study of Active Controlled Tocilizumab Monotherapy for Rheumatoid Arthritis Patients with an Inadequate Response to Methotrexate (SATORI): Significant Reduction in Disease Activity and Serum Vascular Endothelial Growth Factor by IL-6 Receptor Inhibition Th", Modern Rheumatology, vol. 19, No. 1, pp. 12-19.
Non-Final Office Action received for U.S. Appl. No. 13/648,521, dated Jul. 3, 2014, 11 Pages.
Non-Final Office Action received for U.S. Appl. No. 13/648,521, dated Jun. 26, 2015, 9 Pages.
Non-Final Office Action received for U.S. Appl. No. 13/648,521, dated Mar. 19, 2015, 8 Pages.
Non-Final Office Action received for U.S. Appl. No. 13/648,521, dated Oct. 18, 2013, 10 Pages.
Non-Final Office Action received for U.S. Appl. No. 14/350,973, dated Feb. 5, 2016, 17 Pages.
Notice of Allowance received for U.S. Appl. No. 14/350,973, dated Jun. 14, 2016, 8 Pages.
Non-Final Office Action received for U.S. Appl. No. 14/350,973, dated Oct. 18, 2019, 10 Pages.
Nussenblatt, et al. (Apr. 1985) "Standardization of Vitreal Inflammatory Activity in Intermediate and Posterior Uveitis", Ophthalmology, vol. 92, No. 4, pp. 467-471.
Ongkosuwito, et al. (Dec. 1998) "Analysis of Immunoregulatory Cytokines in Ocular Fluid Samples from Patients with Uveitis", Investigative Ophthalmology & Visual Science, vol. 39, No. 13, pp. 2659-2665.
Panka, et al. (May 1988) "Variable Region Framework Differences Result in Decreased or Increased Affinity of Variant Anti-Digoxin Antibodies", Proceedings of the National Academy of Sciences of the United States of America, vol. 85, pp. 3080-3084.
Paul-Pletzer (2006) "Tocilizumab: Blockade of Interleukin-6 Signaling Pathway as A Therapeutic Strategy for Inflammatory Disorders", Drugs of Today, vol. 42, No. 9, pp. 559-576.
Perez, et al. (Sep. 2004) "Elevated Levels of Interleukin 6 in the Vitreous Fluid of Patients with Pars Planitis And Posterior Uveitis: The Massachusetts Eye & Ear Experience and Review of Previous Studies", Ocular Immunology and Inflammation, vol. 12, No. 3, pp. 193-201.
Powchik (Jul. 15, 2010) "Investor Day", Regeneron Pharmaceuticals, pp. 1-19.
Powell, et al. (Sep.-Oct. 1998) "Compendium of Excipients for Parenteral Formulations", PDA Journal of Pharmaceutical Science and Technology, vol. 52, No. 5, pp. 238-311.
Presta (2006) "Engineering of Therapeutic Antibodies to Minimize Immunogenicity and Optimize Function", Advanced Drug Delivery Reviews, pp. 640-656.
Radin, et al. (Jan. 1, 2010) "Safety and Effects on Markers of Inflammation of Subcutaneously Administered regn88/sar153191 (regn88), an Interleukin-6 Receptor Inhibitor, in Patients with Rheumatoid Arthritis: Findings from Phase 1 Studies", Annals of the Rheumatic Diseases, vol. 69, Supplement 3, XP008158577, 99 Page.
Radin, et al. (Nov. 2010) "REGN88/SAR153191, a fully-human interleukin-6 receptor monoclonal antibody, reduces acute phase reactants in patients with rheumatoid arthritis: preliminary observations from Phase 1 studies.", Arthritis & Rheumatology, vol. 62, Supplement 10, XP008158581, p. S1121.
Rafique, et al. (Jun. 23, 2013) "Evaluation of The Binding Kinetics and Functional Bioassay Activity of Sarilumab And Tocilizumab to The Human IL-6 Receptor (IL-6r) alpha", Annals of the Rheumatic Diseases, vol. 72, Issue Suppl 3, pp. A797.1-A797.
Regeneron (Jun. 12, 2014) "Sanofi and Regeneron Announce New, Detailed Data from Positive Sarilumab Phase 3 Rheumatoid Arthritis Trial at EULAR".
Regeneron (Nov. 22, 2013) "Sanofi and Regeneron Report Positive Results with Sarilumab in First Phase 3 Rheumatoid Arthritis Registration Trial", Press Release, Acquire Media, Retrieved From: <<https://investor.regeneron.com/news-releases/news-release-details/sanofi-and-regeneron-report-positive-results-sarilumab-first>>, 6 pages.
Regeneron Pharmaceuticals (Jul. 12, 2011) "Evaluation of Sarilumab (SAR153191/REGN88) on Top of Methotrexate in Rheumatoid Arthritis Patients (RA-MOBILITY)", Retrieved from the internet from URL <<https://clinicaltrials.gov/ct2/results?term=SAR+153191=mobility>>.
Regeneron Pharmaceuticals (Jul. 12, 2011) "Sanofi and Regeneron Report Positive Phase 2b Trial Results with Sarilumab in Rheumatoid Arthritis", Acquire Media, Retrieved form URL: <http://web.archive.org/web/20110818152737/http://investorregeneron.com/releasedetail.cfm?ReleaseiD=590869>>, 3 pages.
Reichert, Janice M. (Jan.-Feb. 2011) "Antibody-Based Therapeutics to Watch in 2011", MABS, vol. 3, No. 1, pp. 76-99.
Restriction Requirement received for U.S. Appl. No. 13/648,521, dated Jun. 10, 2013, 7 Pages.
Restriction Requirement received for U.S. Appl. No. 14/350,973, dated Aug. 19, 2015, 8 Pages.
Rose-John, et al. (May 17, 2006) "Interleukin-6 Biology is Coordinated by Membrane-Bound and Soluble Receptors: Role in Inflammation and Cancer", Journal of Leukocyte Biology, vol. 80, No. 2, pp. 227-236.
Rudikoff, et al. (Mar. 1, 1982) "Single Amino Acid Substitution Altering Antigen-Binding Specificity", Proceedings of the National Academy of Sciences of the United States of America, vol. 79, pp. 1979-1983.
Sanofi (Feb. 2, 2010) "Evaluation of Sarilumab (SAR153191/REGN88) on Top of Methotrexate in Rheumatoid Arthritis Patients (RA-MOBILITY)", Clinical Trials.gov, Retrieved from: <<http://clinicaltrials.gov/show/NCT01061736>>, 6 pages.
Sanofi (Nov. 7, 2013) "View of NCT01061736 on Nov. 7, 2013: ClinicaiTrials.gov Archive", Retrieved from URL: <<https://clinicaltrials.gov/archive/NCT01061736/2013_11_07>>.
Sanofi (Oct. 7, 2010) "Effect of SAR153191 (REGN88) With Methotrexate in Patients with Active Rheumatoid Arthritis Who Failed TNF-α Blockers", ClinicaiTrials.gov, Retrieved from: <<http://clinicaltrials.gov/show/NCT01217814>>, 5 pages.
Sanofi (Sep. 27, 2011) "View of NCT01217814 on Sep. 27, 2011", ClinicaiTrials.gov, Retrieved from URL: <<https://clinicaltrials.gov/archive/NCT01217814/2011_09_27>>, 4 pages.
Sanofi and Regeneron (May 21, 2015) "Sanofi and Regeneron Announce Positive Topline Results from Phase 3 Studies with Sarilumab in Patients with Rheumatoid Arthritis", Press Release, Retrieved from http://mediaroom.sanofi.com/sanofi-and-regeneron-announce-positive-topline-results-from-phase-3-studies-witharilumab-in-patients-with-rheumatoid-arthritis-2, 4 pages.

(56) References Cited

OTHER PUBLICATIONS

Sanofi and Regeneron (Nov. 8, 2015) "Regeneron and Sanofi Present Results from Pivotal Phase 3 Study of Sarilumab at American College of Rheumatology Annual Meeting", Press Release, Regeneron Pharmaceuticals, Inc. Retrieved from http://investor.regeneron.com/releasedetail.cfm?releaseid=941387.

Schulten, et al. (1996) "Recent Developments in the Treatment of Posterior Uveitis", Ocular Immunology and Inflammation, vol. 4, No. 4, pp. 207-217.

Smolen, et al. (Mar. 22-28, 2008) "Effect of Interleukin-6 Receptor Inhibition with Tocilizumab in Patients with Rheumatoid Arthritis (Option Study): A Double-Blind, Placebo-Controlled, Randomised Trial", The Lancet, vol. 371, Issue 9617, pp. 987-997.

Strand, et al. (2012) "Health-related Quality of Life Outcomes of Adalimumab for Patients with Early Rheumatoid Arthritis: Results from a Randomized Multicenter Study", The Journal of Rheumatology, vol. 39, pp. 63-72.

Taylor, Peter C. (Jun. 2010) "Pharmacology of TNF Blockade in Rheumatoid Arthritis and Other Chronic Inflammatory Diseases", Current Opinion in Pharmacology, vol. 10, Issue 3, pp. 308-315.

The Chemical Abstracts Service CAS, 1189541-98-7.

Uchiyama, et al. (2008) "Tocilizumab, A Humanized Anti-Interleukin-6 Receptor Antibody, Ameliorates Joint Swelling in Established Monkey Collagen-Induced Arthritis", Biological and Pharmaceutical Bulletin, vol. 31, No. 6, pp. 1159-1163.

U.S. Adopted Names Council "Statement on a Nonproprietary Name Adopted by the USAN Council: Sarilumab", CAS Registry No. 1189541-98-7.

Valentincic, et al. (Jul. 20, 2011) "Intraocular and Serum Cytokine Profiles in Patients with Intermediate Uveitis", Molecular Vision, vol. 17, pp. 2003-2010.

Vasanthi, et al. (Dec. 2007) "Role of Tumor Necrosis Factor-Alpha in Rheumatoid Arthritis: A Review", APLAR Journal of Rheumatology, vol. 10, No. 4, pp. 270-274.

Whalley, et al. (1997) "Quality of Life in Rheumatoid Arthritis", British Journal of Rheumatology, vol. 36, pp. 884-888.

WHO (Dec. 9, 2004) "International Nonproprietary Names for Pharmaceutical Substances (INN)", WHO Drug Information vol. 25, No. 4, 20 pages.

Wiens, et al. (Jun. 2010) "A Systematic Review and Meta-Analysis of the Efficacy and Safety of Adalimumab for Treating Rheumatoid Arthritis", Rheumatology International, vol. 30, Issue 8, pp. 1063-1070.

Wu, et al. (Apr. 5, 1987) "Receptor-Mediated In Vitro Gene Transformation by a Soluble DNA Carrier System", Journal of Biological Chemistry, vol. 262, No. 10, pp. 4429-4432.

Yoshimura, et al. (2009) "Comprehensive Analysis of Inflammatory Immune Mediators in Vitreoretinal Diseases", PLoS One, vol. 4, No. 12, pp. 1-9.

STABILIZED FORMULATIONS CONTAINING ANTI-INTERLEUKIN-6 RECEPTOR (IL-6R) ANTIBODIES

CROSS-REFERENCE TO RELATED APPLICATIONS

This application is a continuation of U.S. application Ser. No. 14/861,565, filed Sep. 22, 2015, now U.S. Pat. No. 10,072,086, which is a continuation of U.S. application Ser. No. 12/986,223, filed Jan. 7, 2011, now U.S. Pat. No. 9,173,880, which claims the benefit under 35 USC 119(e) of U.S. Application No. 61/293,227, filed Jan. 8, 2010, each of which is incorporated herein by reference in its entirety.

REFERENCE TO A SEQUENCE LISTING

This application includes an electronic sequence listing in a file named "6013US03-Sequence.txt", created on Aug. 9, 2018 and containing 37,508 bytes, which is hereby incorporated by reference in its entirety for all purposes.

FIELD OF THE INVENTION

The present invention relates to the field of therapeutic antibody formulations. More specifically, the present invention relates to the field of pharmaceutical formulations comprising a human antibody that specifically binds to human interleukin-6 receptor.

BACKGROUND

Therapeutic macromolecules (e.g., antibodies) must be formulated in a manner that not only makes the molecules suitable for administration to patients, but also maintains their stability during storage. For example, therapeutic antibodies in liquid solution are prone to degradation, aggregation and/or undesired chemical modifications unless the solution is formulated properly. The stability of an antibody in liquid formulation depends not only on the kinds of excipients used in the formulation, but also on the amounts and proportions of the excipients relative to one another. Furthermore, other considerations aside from stability must be taken into account when preparing a liquid antibody formulation. Examples of such additional considerations include the viscosity of the solution and the concentration of antibody that can be accommodated by a given formulation. Thus, when formulating a therapeutic antibody, great care must be taken to arrive at a formulation that remains stable, contains an adequate concentration of antibody, and possesses a suitable viscosity as well as other properties which enable the formulation to be conveniently administered to patients.

Antibodies to the human interleukin-6 receptor (hIL-6R) are one example of a therapeutically relevant macromolecule that requires proper formulation. Anti-hIL-6R antibodies are clinically useful for the treatment and/or prevention of diseases such as rheumatoid arthritis, ankylosing spondylitis, and other conditions. Exemplary anti-IL-6R antibodies are described, inter alia, in U.S. Pat. Nos. 7,582,298; 6,410,691; 5,817,790; 5,795,695; and 6,670,373. A particularly important anti-hIL-6R antibody with great therapeutic potential is the antibody referred to in U.S. Pat. No. 7,582,298 as VQ8F11-21 (also referred to herein as "mAb1").

Although anti-hIL-6R antibodies are known, there remains a need in the art for novel pharmaceutical formulations comprising anti-hIL-6R antibodies which are sufficiently stable and also suitable for administration to patients.

BRIEF SUMMARY OF THE INVENTION

The present invention satisfies the aforementioned need by providing pharmaceutical formulations comprising a human antibody that specifically binds to human interleukin-6 receptor (hIL-6R). The formulations of the invention may comprise excipients in addition to the anti-hIL-6R antibody. For example, in certain embodiments, the formulation may comprise (i) a human antibody that specifically binds to hIL-6R; (ii) at least one amino acid; and (iii) at least one carbohydrate. The amino acid can be, e.g., histidine and/or arginine. The carbohydrate can be a sugar such as, e.g., sucrose, glucose, mannitol, lactose or trehalose.

According to certain embodiments of the present invention, the formulation further comprises a non-ionic surfactant. The non-ionic surfactant can be, e.g., polysorbate 20, polysorbate 80, polyoxyethylene sorbitan monooleate, polyethylene glycol, etc.

The antibody contained within the pharmaceutical formulations of the present invention can be any antibody which specifically binds to hIL-6R. Exemplary antibodies that may be contained within the formulations of the invention are antibodies comprising a heavy chain variable region (HCVR) and a light chain variable region (LCVR), wherein the HCVR comprises a heavy chain complementary determining region (HCDR) 1 having the amino acid sequence of SEQ ID NO: 20, a HCDR2 having the amino acid sequence of SEQ ID NO:22, and a HCDR3 having the amino acid sequence of SEQ ID NO:24; and wherein the LCVR comprises a light chain complementary determining region (LCDR) 1 having the amino acid sequence of SEQ ID NO: 28, a LCDR2 having the amino acid sequence of SEQ ID NO:30, and a LCDR3 having the amino acid sequence of SEQ ID NO:32. In certain embodiments, the antibody contained within the formulations of the present invention are antibodies comprising a HCVR having the amino acid sequence of SEQ ID NO:18 and a LCVR having the amino acid sequence of SEQ ID NO:26.

The antibody formulations of the present invention may be contained within any suitable container useful for storing pharmaceutical formulations. Examples of such suitable containers include, e.g., glass or plastic vials, syringes and cartridges. The container may be clear or opaque (e.g., amber colored).

According to certain aspects of the present invention, the pharmaceutical formulations remain relatively stable following storage for several days, months or years at a given temperature. For example, in certain exemplary embodiments of the present invention, a high percentage of the antibody (e.g., 90%, 95%, 96% or more) is maintained in its native form following at least 3, 6, 9 or more months of storage. The percentage of native form of the antibody may be measured, e.g., by SE-HPLC, or by any other method known in the art. The storage temperature at which stability of the antibody is maintained can be, e.g., −80° C., −40° C., −20° C., 0° C., 5° C., 25° C., 45° C., or higher.

Other embodiments of the present invention will become apparent from a review of the ensuing detailed description.

DETAILED DESCRIPTION

Figure 1:
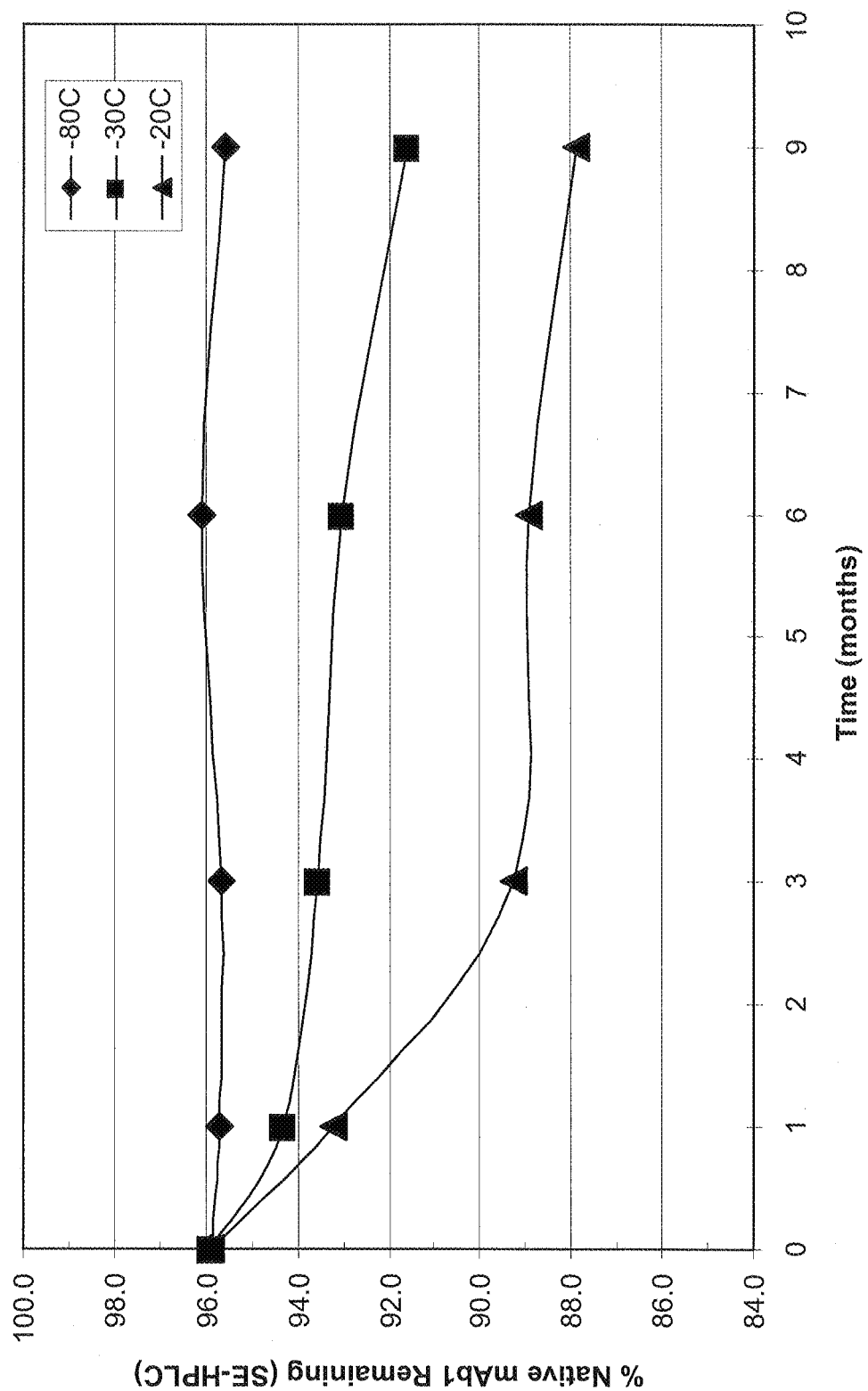
FIG. 1 shows the percent of native mAb1 remaining, as measured by SE-HPLC, following various amounts of time of storage at −20° C. (filled triangles), −30° C. (filled squares), and −80° C. (filled diamonds).

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, the preferred methods and materials are now described. All publications mentioned herein are incorporated herein by reference to describe in their entirety.

Pharmaceutical Formulations

As used herein, the expression "pharmaceutical formulation" means a combination of at least one active ingredient (e.g., a small molecule, macromolecule, compound, etc. which is capable of exerting a biological effect in a human or non-human animal), and at least one inactive ingredient which, when combined with the active ingredient and/or one or more additional inactive ingredients, is suitable for therapeutic administration to a human or non-human animal. The term "formulation," as used herein, means "pharmaceutical formulation" unless specifically indicated otherwise. The present invention provides pharmaceutical formulations comprising at least one therapeutic polypeptide. According to certain embodiments of the present invention, the therapeutic polypeptide is an antibody that binds specifically to human interleukin-6 receptor (hIL-6R) or an antigen-binding fragment thereof. More specifically, the present invention includes pharmaceutical formulations that comprise: (i) a human antibody that specifically binds to hIL-6R; (ii) histidine; and (iii) a carbohydrate. Additional components may be included in the formulations of the present invention such as, e.g., at least one non-ionic surfactant, and at least one additional amino acid. Specific exemplary components and formulations included within the present invention are described in detail below.

The pharmaceutical formulations of the present invention may, in certain embodiments, be fluid formulations. As used herein, the expression "fluid formulation" means a mixture of at least two components that exists predominantly in the fluid state at about 5° C. to about 45° C. Fluid formulations include, inter alia, liquid formulations. Fluid formulations may be of low, moderate or high viscosity depending on their particular constituents.

Antibodies that Bind Specifically to hIL-6R

The pharmaceutical formulations of the present invention may comprise a human antibody, or an antigen-binding fragment thereof, that binds specifically to hIL-6R. As used herein, the term "hIL-6R" means a human cytokine receptor that specifically binds interleukin-6 (IL-6). In certain embodiments, the antibody contained within the pharmaceutical formulations of the present invention binds specifically to the extracellular domain of hIL-6R. The extracellular domain of hIL-6R is represented by the amino acid sequence of SEQ ID NO:74.

The term "antibody", as used herein, is generally intended to refer to immunoglobulin molecules comprising four polypeptide chains, two heavy (H) chains and two light (L) chains inter-connected by disulfide bonds, as well as multimers thereof (e.g., IgM); however, immunoglobulin molecules consisting of only heavy chains (i.e., lacking light chains) are also encompassed within the definition of the term "antibody." Each heavy chain comprises a heavy chain variable region (abbreviated herein as HCVR or VH) and a heavy chain constant region. The heavy chain constant region comprises three domains, CH1, CH2 and CH3. Each light chain comprises a light chain variable region (abbreviated herein as LCVR or VL) and a light chain constant region. The light chain constant region comprises one domain (CL1). The VH and VL regions can be further subdivided into regions of hypervariability, termed complementary determining regions (CDRs), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4.

Unless specifically indicated otherwise, the term "antibody," as used herein, shall be understood to encompass complete antibody molecules as well as antigen-binding fragments thereof. The term "antigen-binding portion" or "antigen-binding fragment" of an antibody (or simply "antibody portion" or "antibody fragment"), as used herein, refers to one or more fragments of an antibody that retain the ability to specifically bind to hIL-6R.

An "isolated antibody", as used herein, is intended to refer to an antibody that is substantially free of other antibodies having different antigenic specificities (e.g., an isolated antibody that specifically binds hIL-6R is substantially free of antibodies that specifically bind antigens other than hIL-6R).

The term "specifically binds," or the like, means that an antibody or antigen-binding fragment thereof forms a complex with an antigen that is relatively stable under physiologic conditions. Specific binding can be characterized by a dissociation constant of at least about $1 \times 10^{-6}$ M or greater. Methods for determining whether two molecules specifically bind are well known in the art and include, for example, equilibrium dialysis, surface plasmon resonance, and the like. An isolated antibody that specifically binds hIL-6R may, however, have cross-reactivity to other antigens, such as IL-6R molecules from other species. In the context of the present invention, multispecific (e.g., bispecific) antibodies that bind to hIL-6R as well as one or more additional antigens are deemed to "specifically bind" hIL-6R. Moreover, an isolated antibody may be substantially free of other cellular material and/or chemicals.

Exemplary anti-hIL-6R antibodies that may be included in the pharmaceutical formulations of the present invention are set forth in U.S. Pat. No. 7,582,298, the disclosure of which is incorporated by reference in its entirety.

According to certain embodiments of the present invention, the anti-hIL-6R antibody, or antigen-binding fragment thereof, comprises a heavy chain complementary determining region (HCDR) 1 having an amino acid sequence selected from the group consisting of SEQ ID NO: 4, 20, 36 and 52; a HCDR2 having an amino acid sequence selected from the group consisting of SEQ ID NO:6, 22, 38 and 54; and a HCDR3 having an amino acid sequence selected from the group consisting of SEQ ID NO:2, 18, 34 and 50. In certain embodiments, the anti-hIL-6R antibody, or antigen-binding fragment thereof, comprises HCDR1-HCDR2-HCDR3 domains, respectively, selected from the group consisting of: (i) SEQ ID NOs:4-6-8; (ii) SEQ ID NOs:20-22-24; (iii) SEQ ID NOs:36-38-40; and (iv) SEQ ID NOs: 52-54-56.

According to certain embodiments of the present invention, the anti-hIL-6R antibody, or antigen-binding fragment thereof, comprises a light chain complementary determining region (LCDR) 1 having an amino acid sequence selected from the group consisting of SEQ ID NO: 12, 28, 44 and 60; a LCDR2 having an amino acid sequence selected from the group consisting of SEQ ID NO:14, 30, 46 and 62; and a LCDR3 having an amino acid sequence selected from the group consisting of SEQ ID NO:16, 32, 48 and 64. In certain embodiments, the anti-hIL-6R antibody, or antigen-binding fragment thereof, comprises LCDR1-LCDR2-LCDR3 domains, respectively, selected from the group consisting of: (i) SEQ ID NOs:12-14-16; (ii) SEQ ID NOs:28-30-32; (iii) SEQ ID NOs:44-46-48; and (iv) SEQ ID NOs:60-62-64.

In certain embodiments, the anti-hIL-6R antibody, or antigen-binding fragment thereof, comprises HCDR1-HCDR2-HCDR3/LCDR1-LCDR2-LCDR3 domains, respectively, selected from the group consisting of: (i) SEQ ID NOs:4-6-8/SEQ ID NOs:12-14-16; (ii) SEQ ID NOs:20-22-24/SEQ ID NOs:28-30-32; (iii) SEQ ID NOs:36-38-40/SEQ ID NOs:44-46-48; and (iv) SEQ ID NOs:52-54-56/SEQ ID NOs:60-62-64.

In certain embodiments, the anti-hIL-6R antibody, or antigen-binding fragment thereof, comprises a heavy chain variable region (HCVR) having an amino acid sequence selected from the group consisting of SEQ ID NO:2, 18, 34 and 50. In certain embodiments, the anti-hIL-6R antibody, or antigen-binding fragment thereof, comprises a light chain variable region (LCVR) having an amino acid sequence selected from the group consisting of SEQ ID NO:10, 26, 42 and 58. In certain embodiments, the anti-hIL-6R antibody, or antigen-binding fragment thereof, comprises a HCVR/LCVR amino acid sequence pair selected from the group consisting of SEQ ID NO:2/10; 18/26; 34/42 and 50/58.

The non-limiting, exemplary antibody used in the Examples herein is referred to as "mAb1." This antibody is also referred to in U.S. Pat. No. 7,582,298 as VQ8F11-21. mAb1 (VQ8F11-21) comprises an HCVR/LCVR amino acid sequence pair having SEQ ID NOs:18/26, and HCDR1-HCDR2-HCDR3/LCDR1-LCDR2-LCDR3 domains represented by SEQ ID NOs:20-22-24/SEQ ID NOs:28-30-32.

The amount of antibody, or antigen-binding fragment thereof, contained within the pharmaceutical formulations of the present invention may vary depending on the specific properties desired of the formulations, as well as the particular circumstances and purposes for which the formulations are intended to be used. In certain embodiments, the pharmaceutical formulations may contain about 1 mg/mL to about 500 mg/mL of antibody; about 5 mg/mL to about 400 mg/mL of antibody; about 5 mg/mL to about 200 mg/mL of antibody; about 25 mg/mL to about 180 mg/mL of antibody; about 25 mg/mL to about 150 mg/mL of antibody; or about 50 mg/mL to about 180 mg/mL of antibody. For example, the formulations of the present invention may comprise about 1 mg/mL; about 2 mg/mL; about 5 mg/mL; about 10 mg/mL; about 15 mg/mL; about 20 mg/mL; about 25 mg/mL; about 30 mg/mL; about 35 mg/mL; about 40 mg/mL; about 45 mg/mL; about 50 mg/mL; about 55 mg/mL; about 60 mg/mL; about 65 mg/mL; about 70 mg/mL; about 75 mg/mL; about 80 mg/mL; about 85 mg/mL; about 86 mg/mL; about 87 mg/mL; about 88 mg/mL; about 89 mg/mL; about 90 mg/mL; about 95 mg/mL; about 100 mg/mL; about 105 mg/mL; about 110 mg/mL; about 115 mg/mL; about 120 mg/mL; about 125 mg/mL; about 130 mg/mL; about 131 mg/mL; about 132 mg/mL; about 133 mg/mL; about 134 mg/mL; about 135 mg/mL; about 140 mg/mL; about 145 mg/mL; about 150 mg/mL; about 155 mg/mL; about 160 mg/mL; about 165 mg/mL; about 170 mg/mL; about 175 mg/mL; about 180 mg/mL; about 185 mg/mL; about 190 mg/mL; about 195 mg/mL; or about 200 mg/mL of an antibody or an antigen-binding fragment thereof, that binds specifically to hIL-6R.

Excipients and pH

The pharmaceutical formulations of the present invention comprise one or more excipients. The term "excipient," as used herein, means any non-therapeutic agent added to the formulation to provide a desired consistency, viscosity or stabilizing effect.

In certain embodiments, the pharmaceutical formulation of the invention comprises at least one amino acid. Exemplary amino acids suitable for use in the formulations of the present invention include, inter alia, arginine and/or histidine.

The amount of amino acid contained within the pharmaceutical formulations of the present invention may vary depending on the specific properties desired of the formulations, as well as the particular circumstances and purposes for which the formulations are intended to be used. In certain embodiments, the formulations may contain about 1 mM to about 200 mM of an amino acid; about 2 mM to about 100 mM of an amino acid; about 5 mM to about 50 mM of an amino acid; or about 10 mM to about 25 mM of an amino acid. For example, the pharmaceutical formulations of the present invention may comprise about 1 mM; about 1.5 mM; about 2 mM; about 2.5 mM; about 3 mM; about 3.5 mM; about 4 mM; about 4.5 mM; about 5 mM; about 5.5 mM; about 6 mM; about 6.5 mM; about 7 mM; about 7.5 mM; about 8 mM; about 8.5 mM; about 9 mM; about 9.5 mM; about 10 mM; about 10.5 mM; about 11 mM; about 11.5 mM; about 12 mM; about 12.5 mM; about 13 mM; about 13.5 mM; about 14 mM; about 14.5 mM; about 15 mM; about 15.5 mM; 16 mM; about 16.5 mM; about 17 mM; about 17.5 mM; about 18 mM; about 18.5 mM; about 19 mM; about 19.5 mM; about 20 mM; about 20.5 mM; about 21 mM; about 21.5 mM; about 22 mM; about 22.5 mM; about 23 mM; about 23.5 mM; about 24 mM; about 24.5 mM; about 25 mM; about 25.5 mM; about 26 mM; about 26.5 mM; about 27 mM; about 27.5 mM; about 28 mM; about 28.5 mM; about 29 mM; about 29.5 mM; about 30 mM; about 35 mM; about 40 mM; about 45 mM; or about 50 mM of an amino acid (e.g., histidine and/or arginine).

The pharmaceutical formulations of the present invention may also comprise one or more carbohydrate, e.g., one or more sugar. The sugar can be a reducing sugar or a non-reducing sugar. "Reducing sugars" include, e.g., sugars with a ketone or aldehyde group and contain a reactive hemiacetal group, which allows the sugar to act as a reducing agent. Specific examples of reducing sugars include fructose, glucose, glyceraldehyde, lactose, arabinose, mannose, xylose, ribose, rhamnose, galactose and maltose. Non-reducing sugars can comprise an anomeric carbon that is an acetal and is not substantially reactive with amino acids or polypeptides to initiate a Maillard reaction. Specific examples of non-reducing sugars include sucrose, trehalose, sorbose, sucralose, melezitose and raffinose. Sugar acids include, for example, saccharic acids, gluconate and other polyhydroxy sugars and salts thereof.

The amount of sugar contained within the pharmaceutical formulations of the present invention will vary depending on the specific circumstances and intended purposes for which the formulations are used. In certain embodiments, the formulations may contain about 0.1% to about 20% sugar; about 0.5% to about 20% sugar; about 1% to about 20% sugar; about 2% to about 15% sugar; about 3% to about 10% sugar; about 4% to about 10% sugar; or about 5% to about 10% sugar. For example, the pharmaceutical formulations of the present invention may comprise about 0.5%; about 1.0%; about 1.5%; about 2.0%; about 2.5%; about 3.0%; about 3.5%; about 4.0%; about 4.5%; about 5.0%; about 5.5%; about 6.0%; 6.5%; about 7.0%; about 7.5%; about 8.0%; about 8.5%; about 9.0%; about 9.5%; about 10.0%; about 10.5%; about 11.0%; about 11.5%; about 12.0%; about 12.5%; about 13.0%; about 13.5%; about 14.0%; about 14.5%; about 15.0%; about 15.5%; about 16.0%; 16.5%; about 17.0%; about 17.5%; about 18.0%; about 18.5%; about 19.0%; about 19.5%; or about 20.0% sugar (e.g., sucrose).

The pharmaceutical formulations of the present invention may also comprise one or more surfactant. As used herein, the term "surfactant" means a substance which reduces the surface tension of a fluid in which it is dissolved and/or reduces the interfacial tension between oil and water. Surfactants can be ionic or non-ionic. Exemplary non-ionic surfactants that can be included in the formulations of the present invention include, e.g., alkyl poly(ethylene oxide), alkyl polyglucosides (e.g., octyl glucoside and decyl maltoside), fatty alcohols such as cetyl alcohol and oleyl alcohol, cocamide MEA, cocamide DEA, and cocamide TEA. Specific non-ionic surfactants that can be included in the formulations of the present invention include, e.g., polysorbates such as polysorbate 20, polysorbate 28, polysorbate 40, polysorbate 60, polysorbate 65, polysorbate 80, polysorbate 81, and polysorbate 85; poloxamers such as poloxamer 188, poloxamer 407; polyethylene-polypropylene glycol; or polyethylene glycol (PEG). Polysorbate 20 is also known as TWEEN 20, sorbitan monolaurate and polyoxyethylenesorbitan monolaurate.

The amount of surfactant contained within the pharmaceutical formulations of the present invention may vary depending on the specific properties desired of the formulations, as well as the particular circumstances and purposes for which the formulations are intended to be used. In certain embodiments, the formulations may contain about 0.05% to about 5% surfactant; or about 0.1% to about 0.2% surfactant. For example, the formulations of the present invention may comprise about 0.05%; about 0.06%; about 0.07%; about 0.08%; about 0.09%; about 0.10%; about 0.11%; about 0.12%; about 0.13%; about 0.14%; about 0.15%; about 0.16%; about 0.17%; about 0.18%; about 0.19%; about 0.20%; about 0.21%; about 0.22%; about 0.23%; about 0.24%; about 0.25%; about 0.26%; about 0.27%; about 0.28%; about 0.29%; or about 0.30% surfactant (e.g., polysorbate 20).

The pharmaceutical formulations of the present invention may have a pH of from about 5.0 to about 8.0. For example, the formulations of the present invention may have a pH of about 5.0; about 5.2; about 5.4; about 5.6; about 5.8; about 6.0; about 6.2; about 6.4; about 6.6; about 6.8; about 7.0; about 7.2; about 7.4; about 7.6; about 7.8; or about 8.0.

Exemplary Formulations

According to one aspect of the present invention, the pharmaceutical formulation comprises: (i) a human antibody that specifically binds to hIL-6R (e.g., mAb1); (ii) an amino acid (e.g., histidine); and (iii) a sugar (e.g., sucrose). Specific, non-limiting exemplary embodiments encompassed by this aspect of the invention are set forth in Table 1.

TABLE 1

Exemplary Pharmaceutical Formulations Comprising mAb1, Histidine and Sucrose

| | | | | | | | | | | | | | | | | |
|---|---|---|---|---|---|---|---|---|---|---|---|---|---|---|---|---|
| mAb1 (mg/ml) | 25 | 50 | 100 | 150 | 25 | 50 | 100 | 150 | 25 | 50 | 100 | 150 | 25 | 50 | 100 | 150 |
| histidine (mM) | 10 | 10 | 10 | 10 | 10 | 10 | 10 | 10 | 10 | 10 | 10 | 10 | 10 | 10 | 10 | 10 |
| sucrose (%) | 1 | 1 | 1 | 1 | 2 | 2 | 2 | 2 | 4 | 4 | 4 | 4 | 6 | 6 | 6 | 6 |

According to another aspect of the present invention, the pharmaceutical formulation comprises: (i) a human antibody that specifically binds to hIL-6R (e.g., mAb1); (ii) an amino acid (e.g., histidine); (iii) a sugar (e.g., sucrose); and (iv) a surfactant (e.g., polysorbate 20). Specific, non-limiting exemplary embodiments encompassed by this aspect of the invention are set forth in Tables 2A and 2B.

TABLE 2A

Exemplary Pharmaceutical Formulations Comprising mAb1, Histidine, Sucrose and Polysorbate 20

| | | | | | | | | | | | | |
|---|---|---|---|---|---|---|---|---|---|---|---|---|
| mAb1 (mg/ml) | 25 | 50 | 100 | 150 | 25 | 50 | 100 | 150 | 25 | 50 | 100 | 150 |
| histidine (mM) | 10 | 10 | 10 | 10 | 10 | 10 | 10 | 10 | 10 | 10 | 10 | 10 |
| sucrose (%) | 2 | 2 | 2 | 2 | 5 | 5 | 5 | 5 | 10 | 10 | 10 | 10 |
| polysorbate 20 (%) | 0.1 | 0.1 | 0.1 | 0.1 | 0.1 | 0.1 | 0.1 | 0.1 | 0.1 | 0.1 | 0.1 | 0.1 |

TABLE 2B

Exemplary Pharmaceutical Formulations Comprising mAb1, Histidine, Sucrose and Polysorbate 20

| | | | | | | | | | | | | |
|---|---|---|---|---|---|---|---|---|---|---|---|---|
| mAb1 (mg/ml) | 25 | 50 | 100 | 150 | 25 | 50 | 100 | 150 | 25 | 50 | 100 | 150 |
| histidine (mM) | 10 | 10 | 10 | 10 | 10 | 10 | 10 | 10 | 10 | 10 | 10 | 10 |
| sucrose (%) | 2 | 2 | 2 | 2 | 5 | 5 | 5 | 5 | 10 | 10 | 10 | 10 |
| polysorbate 20 (%) | 0.2 | 0.2 | 0.2 | 0.2 | 0.2 | 0.2 | 0.2 | 0.2 | 0.2 | 0.2 | 0.2 | 0.2 |

According to another aspect of the present invention, the pharmaceutical formulation comprises: (i) a human antibody that specifically binds to hIL-6R (e.g., mAb1); (ii) a first amino acid (e.g., histidine); (iii) a sugar (e.g., sucrose); (iv) a surfactant (e.g., polysorbate 20); and (v) a second amino acid (e.g., arginine). Specific, non-limiting exemplary embodiments encompassed by this aspect of the invention are set forth in Tables 3A, 3B, 3C, 3D, 3E and 3F.

TABLE 3A

Exemplary Pharmaceutical Formulations Comprising mAb1, Histidine, Sucrose, Polysorbate 20 and Arginine

| | | | | | | | | | | | | |
|---|---|---|---|---|---|---|---|---|---|---|---|---|
| mAb1 (mg/ml) | 25 | 50 | 100 | 150 | 25 | 50 | 100 | 150 | 25 | 50 | 100 | 150 |
| histidine (mM) | 10 | 10 | 10 | 10 | 10 | 10 | 10 | 10 | 10 | 10 | 10 | 10 |
| sucrose (%) | 2 | 2 | 2 | 2 | 5 | 5 | 5 | 5 | 10 | 10 | 10 | 10 |
| polysorbate 20 (%) | 0.2 | 0.2 | 0.2 | 0.2 | 0.2 | 0.2 | 0.2 | 0.2 | 0.2 | 0.2 | 0.2 | 0.2 |
| arginine (mM) | 10 | 10 | 10 | 10 | 10 | 10 | 10 | 10 | 10 | 10 | 10 | 10 |

TABLE 3B

Exemplary Pharmaceutical Formulations Comprising mAb1, Histidine, Sucrose, Polysorbate 20 and Arginine

| | | | | | | | | | | | | |
|---|---|---|---|---|---|---|---|---|---|---|---|---|
| mAb1 (mg/ml) | 25 | 50 | 100 | 150 | 25 | 50 | 100 | 150 | 25 | 50 | 100 | 150 |
| histidine (mM) | 10 | 10 | 10 | 10 | 10 | 10 | 10 | 10 | 10 | 10 | 10 | 10 |
| sucrose (%) | 2 | 2 | 2 | 2 | 5 | 5 | 5 | 5 | 10 | 10 | 10 | 10 |
| polysorbate 20 (%) | 0.2 | 0.2 | 0.2 | 0.2 | 0.2 | 0.2 | 0.2 | 0.2 | 0.2 | 0.2 | 0.2 | 0.2 |
| arginine (mM) | 25 | 25 | 25 | 25 | 25 | 25 | 25 | 25 | 25 | 25 | 25 | 25 |

TABLE 3C

Exemplary Pharmaceutical Formulations Comprising mAb1, Histidine, Sucrose, Polysorbate 20 and Arginine

| mAb1 (mg/ml) | 25 | 50 | 100 | 150 | 25 | 50 | 100 | 150 | 25 | 50 | 100 | 150 |
|---|---|---|---|---|---|---|---|---|---|---|---|---|
| histidine (mM) | 25 | 25 | 25 | 25 | 25 | 25 | 25 | 25 | 25 | 25 | 25 | 25 |
| sucrose (%) | 2 | 2 | 2 | 2 | 5 | 5 | 5 | 5 | 10 | 10 | 10 | 10 |
| polysorbate 20 (%) | 0.2 | 0.2 | 0.2 | 0.2 | 0.2 | 0.2 | 0.2 | 0.2 | 0.2 | 0.2 | 0.2 | 0.2 |
| arginine (mM) | 10 | 10 | 10 | 10 | 10 | 10 | 10 | 10 | 10 | 10 | 10 | 10 |

TABLE 3D

Exemplary Pharmaceutical Formulations Comprising mAb1, Histidine, Sucrose, Polysorbate 20 and Arginine

| mAb1 (mg/ml) | 25 | 50 | 100 | 150 | 25 | 50 | 100 | 150 | 25 | 50 | 100 | 150 |
|---|---|---|---|---|---|---|---|---|---|---|---|---|
| histidine (mM) | 25 | 25 | 25 | 25 | 25 | 25 | 25 | 25 | 25 | 25 | 25 | 25 |
| sucrose (%) | 2 | 2 | 2 | 2 | 5 | 5 | 5 | 5 | 10 | 10 | 10 | 10 |
| polysorbate 20 (%) | 0.2 | 0.2 | 0.2 | 0.2 | 0.2 | 0.2 | 0.2 | 0.2 | 0.2 | 0.2 | 0.2 | 0.2 |
| arginine (mM) | 25 | 25 | 25 | 25 | 25 | 25 | 25 | 25 | 25 | 25 | 25 | 25 |

TABLE 3E

Exemplary Pharmaceutical Formulations Comprising mAb1, Histidine, Sucrose, Polysorbate 20 and Arginine

| mAb1 (mg/ml) | 25 | 50 | 100 | 150 | 25 | 50 | 100 | 150 | 25 | 50 | 100 | 150 |
|---|---|---|---|---|---|---|---|---|---|---|---|---|
| histidine (mM) | 25 | 25 | 25 | 25 | 25 | 25 | 25 | 25 | 25 | 25 | 25 | 25 |
| sucrose (%) | 2 | 2 | 2 | 2 | 5 | 5 | 5 | 5 | 10 | 10 | 10 | 10 |
| polysorbate 20 (%) | 0.2 | 0.2 | 0.2 | 0.2 | 0.2 | 0.2 | 0.2 | 0.2 | 0.2 | 0.2 | 0.2 | 0.2 |
| arginine (mM) | 50 | 50 | 50 | 50 | 50 | 50 | 50 | 50 | 50 | 50 | 50 | 50 |

TABLE 3F

Exemplary Pharmaceutical Formulations Comprising mAb1, Histidine, Sucrose, Polysorbate 20 and Arginine

| mAb1 (mg/ml) | 160 | 170 | 175 | 180 | 160 | 170 | 175 | 180 | 160 | 170 | 175 | 180 |
|---|---|---|---|---|---|---|---|---|---|---|---|---|
| histidine (mM) | 25 | 25 | 25 | 25 | 25 | 25 | 25 | 25 | 25 | 25 | 25 | 25 |
| sucrose (%) | 2 | 2 | 2 | 2 | 5 | 5 | 5 | 5 | 10 | 10 | 10 | 10 |
| polysorbate 20 (%) | 0.2 | 0.2 | 0.2 | 0.2 | 0.2 | 0.2 | 0.2 | 0.2 | 0.2 | 0.2 | 0.2 | 0.2 |
| arginine (mM) | 50 | 50 | 50 | 50 | 50 | 50 | 50 | 50 | 50 | 50 | 50 | 50 |

Additional non-limiting examples of pharmaceutical formulations encompassed by the present invention are set forth elsewhere herein, including the working Examples presented below.

Stability and Viscosity of the Pharmaceutical Formulations

The pharmaceutical formulations of the present invention typically exhibit high levels of stability. The term "stable," as used herein in reference to the pharmaceutical formulations, means that the antibodies within the pharmaceutical formulations retain an acceptable degree of structure and/or function and/or biological activity after storage for a defined amount of time. A formulation may be stable even though the antibody contained therein does not maintain 100% of its structure and/or function and/or biological activity after storage for a defined amount of time. Under certain circumstances, maintenance of about 80%, about 85%, about 90%, about 95%, about 96%, about 97%, about 98% or about 99% of an antibody's structure and/or function and/or biological activity after storage for a defined amount of time may be regarded as "stable."

Stability can be measured, inter alia, by determining the percentage of native antibody remaining in the formulation after storage for a defined amount of time at a given temperature. The percentage of native antibody can be determined by, inter alia, size exclusion chromatography (e.g., size exclusion high performance liquid chromatography [SE-HPLC]). An "acceptable degree of stability," as that phrase is used herein, means that at least 90% of the native form of the antibody can be detected in the formulation after storage for a defined amount of time at a given temperature. In certain embodiments, at least about 90%, 91%, 92%, 93%, 94%, 95%, 96%, 97%, 98%, 99% or 100% of the native form of the antibody can be detected in the formulation after storage for a defined amount of time at a given temperature. The defined amount of time after which stability is measured can be at least 1 month, at least 2 months, at least 3 months, at least 4 months, at least 5 months, at least 6 months, at least 7 months, at least 8 months, at least 9 months, at least 10 months, at least 11 months, at least 12 months, at least 18 months, at least 24 months, or more. The temperature at which the pharmaceutical formulation may be stored when assessing stability can be any temperature from about −80° C. to about 45° C., e.g., storage at about −30° C., about −20° C., about 0° C., about 5° C., about 25° C., or about 45° C. For example, a pharmaceutical formulation may be deemed stable if after 3 months of storage at 5° C., greater than about 90%, 95%, 96% or 97% of native antibody is detected by SE-HPLC. A pharmaceutical formulation may also be deemed stable if after 6 months of storage at 5° C., greater than about 90%, 95%, 96% or 97% of native antibody is detected by SE-HPLC. A pharmaceutical formulation may also be deemed stable if after 9 months of storage at 5° C., greater than about 90%, 95%, 96% or 97% of native antibody is detected by SE-HPLC. A pharmaceutical formulation may also be deemed stable if after 3 months of storage at 25° C., greater than about 90%, 95%, 96% or 97% of native antibody is detected by SE-HPLC. A pharmaceutical formulation may also be deemed stable if after 6 months of storage at 25° C., greater than about 90%, 95%, 96% or 97% of native antibody is detected by SE-HPLC. A pharmaceutical formulation may also be deemed stable if after 9 months of storage at 25° C., greater than about 90%, 95%, 96% or 97% of native antibody is detected by SE-HPLC.

Other methods may be used to assess the stability of the formulations of the present invention such as, e.g., differential scanning calorimetry (DSC) to determine thermal stability, controlled agitation to determine mechanical stability, and absorbance at about 350 nm or about 405 nm to determine solution turbidities. For example, a formulation of the present invention may be considered stable if, after 6 or more months of storage at about 5° C. to about 25° C., the change in $OD_{405}$ of the formulation is less than about 0.05 (e.g., 0.04, 0.03, 0.02, 0.01, or less) from the $OD_{405}$ of the formulation at t=0.

Stability may also be assessed by measuring the biological activity and/or binding affinity of the antibody to its target. For example, a formulation of the present invention may be regarded as stable if, after storage at e.g., 5° C., 25° C., 45° C., etc. for a defined amount of time (e.g., 1 to 12 months), the anti-IL-6R antibody contained within the formulation binds to IL-6R with an affinity that is at least 50%, 60%, 70%, 80%, 90%, 95%, or more of the binding affinity of the antibody prior to said storage. Additional methods for assessing the stability of an antibody in formulation are demonstrated in the Examples presented below.

In the fluid form, the pharmaceutical formulations of the present invention may, in certain embodiments, exhibit low to moderate levels of viscosity. "Viscosity" as used herein may be "kinematic viscosity" or "absolute viscosity." "Kinematic viscosity" is a measure of the resistive flow of a fluid under the influence of gravity. When two fluids of equal volume are placed in identical capillary viscometers and allowed to flow by gravity, a viscous fluid takes longer than a less viscous fluid to flow through the capillary. For example, if one fluid takes 200 seconds to complete its flow and another fluid takes 400 seconds, the second fluid is twice as viscous as the first on a kinematic viscosity scale. "Absolute viscosity", sometimes called dynamic or simple viscosity, is the product of kinematic viscosity and fluid density (Absolute Viscosity=Kinematic Viscosity×Density). The dimension of kinematic viscosity is $L^2/T$ where L is a length and T is a time. Commonly, kinematic viscosity is expressed in centistokes (cSt). The SI unit of kinematic viscosity is $mm^2/s$, which is 1 cSt. Absolute viscosity is expressed in units of centipoise (cP). The SI unit of absolute viscosity is the milliPascal-second (mPa·s), where 1 cP=1 mPa·s.

As used herein, a low level of viscosity, in reference to a fluid formulation of the present invention, will exhibit an absolute viscosity of less than about 20 cPoise (cP). For example, a fluid formulation of the invention will be deemed to have "low viscosity," if, when measured using standard viscosity measurement techniques, the formulation exhibits an absolute viscosity of about 19 cP, about 18 cP, about 17 cP, about 16 cP, about 15 cP, about 14 cP, about 13 cP, about 12 cP, about 11 cP, about 10 cP, about 9 cP, about 8 cP, about 7 cP, about 6 cP, about 5 cP, about 4 cP, or less. As used herein, a moderate level of viscosity, in reference to a fluid formulation of the present invention, will exhibit an absolute viscosity of between about 30 cP and about 20 cP. For example, a fluid formulation of the invention will be deemed to have "moderate viscosity," if when measured using standard viscosity measurement techniques, the formulation exhibits an absolute viscosity of about 30 cP, about 29 cP, about 28 cP, about 27 cP, about 26 cP, about 25 cP, about 24 cP, about 23 cP, about 22 cP, about 21 cP or about 20 cP.

As illustrated in Example 6 below, the present inventors have made the surprising discovery that low to moderate viscosity fluid formulations comprising high concentrations of an anti-hIL-6R antibody (e.g., up to at least 175 mg/mL) can be obtained by formulating the antibody with 25 mM to 100 mM histidine and 25 mM to 50 mM arginine. In addition, it was further discovered that the viscosity of the formulation could be decreased to an even greater extent by adjusting the sucrose content to less than 10%.

Containers for the Pharmaceutical Formulations and Methods of Administration

The pharmaceutical formulations of the present invention may be contained within any container suitable for storage of medicines and other therapeutic compositions. For example, the pharmaceutical formulations may be contained within a sealed and sterilized plastic or glass container having a defined volume such as a vial, ampule, syringe, cartridge, or bottle. Different types of vials can be used to contain the formulations of the present invention including, e.g., clear and opaque (e.g., amber) glass or plastic vials. Likewise, any type of syringe can be used to contain and/or administer the pharmaceutical formulations of the present invention.

The pharmaceutical formulations of the present invention may be contained within "normal tungsten" syringes or "low tungsten" syringes. As will be appreciated by persons of ordinary skill in the art, the process of making glass syringes generally involves the use of a hot tungsten rod which functions to pierce the glass thereby creating a hole from which liquids can be drawn and expelled from the syringe. This process results in the deposition of trace amounts of tungsten on the interior surface of the syringe. Subsequent washing and other processing steps can be used to reduce the amount of tungsten in the syringe. As used herein, the term "normal tungsten" means that the syringe contains greater than 500 parts per billion (ppb) of tungsten. The term "low tungsten" means that the syringe contains less than 500 ppb of tungsten. For example, a low tungsten syringe, according to the present invention, can contain less than about 490, 480, 470, 460, 450, 440, 430, 420, 410, 390, 350, 300, 250, 200, 150, 100, 90, 80, 70, 60, 50, 40, 30, 20, 10 or fewer ppb of tungsten.

The rubber plungers used in syringes, and the rubber stoppers used to close the openings of vials, may be coated to prevent contamination of the medicinal contents of the syringe or vial and/or to preserve their stability. Thus, pharmaceutical formulations of the present invention, according to certain embodiments, may be contained within a syringe that comprises a coated plunger, or within a vial that is sealed with a coated rubber stopper. For example, the plunger or stopper may be coated with a fluorocarbon film. Examples of coated stoppers and/or plungers suitable for use with vials and syringes containing the pharmaceutical formulations of the present invention are mentioned in, e.g., U.S. Pat. Nos. 4,997,423; 5,908,686; 6,286,699; 6,645,635; and 7,226,554, the contents of which are incorporated by reference herein in their entireties. Particular exemplary coated rubber stoppers and plungers that can be used in the context of the present invention are commercially available under the tradename "FluroTec®," available from West Pharmaceutical Services, Inc. (Lionville, Pa.).

According to certain embodiments of the present invention, the pharmaceutical formulations may be contained within a low tungsten syringe that comprises a fluorocarbon-coated plunger. As discussed in the Examples section below, the combination of a low tungsten syringe and a fluorocarbon-coated plunger was observed to yield surprising stability characteristics with regard to the pharmaceutical formulations of the present invention.

The pharmaceutical formulations can be administered to a patient by parenteral routes such as injection (e.g., subcutaneous, intravenous, intramuscular, intraperitoneal, etc.) or percutaneous, mucosal, nasal, pulmonary and/or oral administration. Numerous reusable pen and/or autoinjector delivery devices can be used to subcutaneously deliver the pharmaceutical formulations of the present invention. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (sanofi-aventis, Frankfurt, Germany), to name only a few. Examples of disposable pen and/or autoinjector delivery devices having applications in subcutaneous delivery of a pharmaceutical composition of the present invention include, but are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L. P.), and the HUMIRA™ Pen (Abbott Labs, Abbott Park, Ill.), to name only a few.

The use of a microinfusor to deliver the pharmaceutical formulations of the present invention is also contemplated herein. As used herein, the term "microinfusor" means a subcutaneous delivery device designed to slowly administer large volumes (e.g., up to about 2.5 mL or more) of a therapeutic formulation over a prolonged period of time (e.g., about 10, 15, 20, 25, 30 or more minutes). See, e.g., U.S. Pat. Nos. 6,629,949; 6,659,982; and Meehan et al., *J. Controlled Release* 46:107-116 (1996). Microinfusors are particularly useful for the delivery of large doses of therapeutic proteins contained within high concentration (e.g., about 100, 125, 150, 175, 200 or more mg/mL) and/or viscous solutions.

Therapeutic Uses of the Pharmaceutical Formulations

The pharmaceutical formulations of the present invention are useful, inter alia, for the treatment, prevention and/or amelioration of any disease or disorder associated with IL-6 activity, including diseases or disorders mediated by activation of the IL-6 receptor. Exemplary, non-limiting diseases and disorders that can be treated and/or prevented by the administration of the pharmaceutical formulations of the present invention include, e.g., rheumatoid arthritis, ankylosing spondylitis, Crohn's disease, ulcerative colitis, pancreatitis, juvenile idiopathic arthritis, vasculitis, Kawasaki disease, systemic lupus erythematosis, psoriasis, psoriatic arthritis, Sjogren syndrome, Still's disease, Castleman's disease, multiple sclerosis, diseases associated with abnormal blood coagulation or fibrinolysis (e.g., thrombosis), cancer (e.g., breast cancer, leukemia, ovarian cancer, melanoma, prostate cancer, pancreatic cancer, lymphoma, lung cancer, renal cell carcinoma, colorectal cancer, multiple myeloma, etc.), cachexia, chronic rejection of transplanted organs and cells, cardiopathy, viral infection (e.g., HIV infection, EBV infection, etc.), plasmacytosis, hyperimmunoglobulinemia, anemia, nephritis, mesothelioma, and hearing loss and other inner ear disorders.

Thus, the present invention includes methods of treating, preventing, and/or ameliorating any disease or disorder associated with IL-6 activity or IL-6R activation (including any of the above mentioned exemplary diseases, disorders and conditions). The therapeutic methods of the present invention comprise administering to a subject any formulation comprising an anti-hIL-6R antibody as disclosed herein. The subject to which the pharmaceutical formulation is administered can be, e.g., any human or non-human animal that is in need of such treatment, prevention and/or amelioration, or who would otherwise benefit from the inhibition or attenuation of IL-6 and/or IL-6R-mediated activity. For example, the subject can be an individual that is diagnosed with, or who is deemed to be at risk of being afflicted by any of the aforementioned diseases or disorders. The present invention further includes the use of any of the pharmaceutical formulations disclosed herein in the manufacture of a medicament for the treatment, prevention and/or amelioration of any disease or disorder associated with IL-6 activity or IL-6R activation (including any of the above mentioned exemplary diseases, disorders and conditions).

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1. Stability of a Fully Human Anti-Human Interleukin-6 Receptor (IL-6R) Antibody ("mAb1") after Storage at Low Temperatures In this Example, various formulations were created containing an anti-human IL-6R antibody without excipients. The exemplary antibody used in this and all subsequent Examples set forth below is an antibody comprising a heavy chain variable region (HCVR) with the amino acid sequence of SEQ ID NO:18, and a light chain variable region (LCVR) with the amino acid sequence of SEQ ID NO:26. This antibody is referred to herein as "mAb1".

As a preliminary experiment, the stability of mAb1 in liquid solution was determined following various amounts of time in frozen storage at −20° C., −30° C. and −80° C. The concentration of mAb1 used in this Example was 128 mg/mL. At various time points, the stability of mAb1 was determined by size exclusion high performance liquid chromatography (SE-HPLC) and by cation exchange high performance liquid chromatography (CEX-HPLC). Stability was assessed based on the percentage of native mAb1 remaining in the sample (by SE-HPLC; Table 4) and by the percentage of acidic species observed in the sample (by CEX-HPLC; Table 5) (An increase in percent acidic species is consistent with deamidation of the antibody and is thus considered an undesired phenomenon with respect to the pharmaceutical formulations of the present invention).

Figure 2:
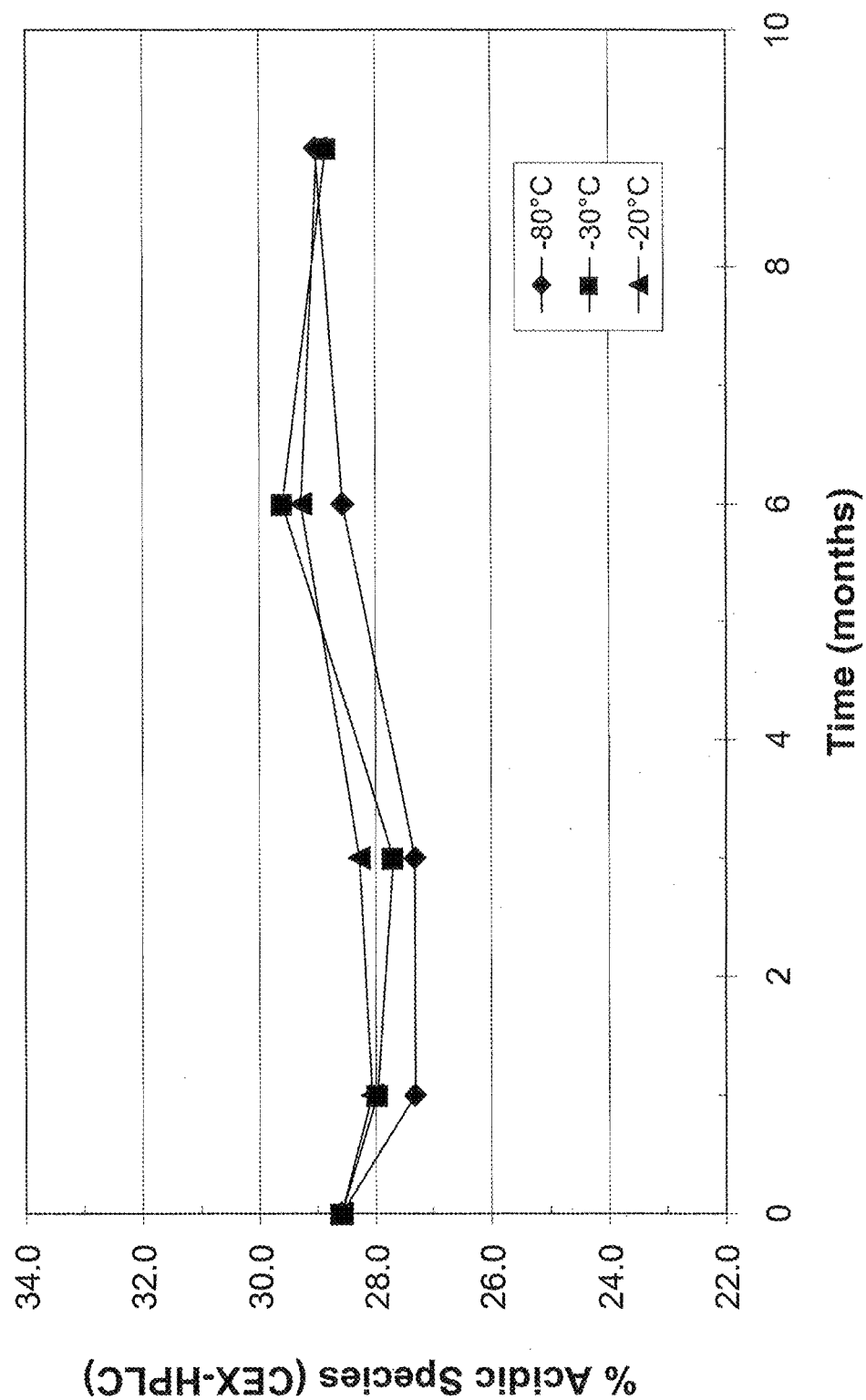
FIG. 2 shows the percent of acidic species of mAb1, as measured by CEX-HPLC, following various amounts of time of storage at −20° C. (filled triangles), −30° C. (filled squares), and −80° C. (filled diamonds).

The results of Tables 3 and 4 are depicted in FIGS. 1 and 2, respectively. These results show that mAb1 can remain stable at a concentration of 128 mg/mL for at least 9 months when stored at −80° C.

TABLE 4

% Native mAb1 Remaining (SE-HPLC)

| Time (months) | Storage Temperature | | |
| --- | --- | --- | --- |
| | −80° C. | −30° C. | −20° C. |
| 0 | 95.9 | 95.9 | 95.9 |
| 1 | 95.7 | 94.3 | 93.2 |
| 3 | 95.6 | 93.6 | 89.3 |
| 6 | 96.1 | 96.0 | 88.9 |
| 9 | 95.6 | 91.6 | 87.9 |

TABLE 5

% Acidic Species (CEX-HPLC)

| Time (months) | Storage Temperature | | |
| --- | --- | --- | --- |
| | −80° C. | −30° C. | −20° C. |
| 0 | 28.6 | 28.6 | 28.6 |
| 1 | 27.3 | 28.0 | 28.1 |
| 3 | 27.3 | 27.7 | 28.3 |
| 6 | 28.6 | 29.6 | 29.3 |
| 9 | 29.0 | 28.8 | 29.0 |

Example 2. Stability of mAb1 Formulations Containing Minimal Excipients

Eight different formulations containing mAb1 and minimal excipients as shown in Table 6 were prepared.

TABLE 6 mAb1 Minimal Excipient Formulations

| Formulation | Excipient | mAb1 (mg/mL) |
| --- | --- | --- |
| 1 | 0.13% polysorbate 20 6% sucrose | 80 |
| 2 | 0.13% polysorbate 20 | 80 |
| 3 | 1% sucrose | 80 |
| 4 | 2% sucrose | 80 |
| 5 | 4% sucrose | 80 |
| 6 | 6% sucrose | 80 |
| 7 | none | 80 |
| 8 | none | 65 |

All formulations contain 10 mM histidine, pH 6.0

The formulations were tested for stability by SE-HPLC after various amounts of time at −30° C. and −20° C. The results, expressed in percent of native mAb1 remaining, are shown in Tables 7 (−30° C. storage) and 8 (−20° C.).

TABLE 7

% Native mAb1 Remaining (SE-HPLC) After Storage at −30° C.

| Time (months) | Formulation # (see Table 6) | | | | | | | |
| --- | --- | --- | --- | --- | --- | --- | --- | --- |
| | 1 | 2 | 3 | 4 | 5 | 6 | 7 | 8 |
| 0 | 96.4 | 96.2 | 96.4 | 96.5 | 96.5 | 96.6 | 96.2 | 96.5 |
| 1 | 96.4 | 95.1 | 96.3 | 96.3 | 96.4 | 96.6 | 95.1 | 95.3 |
| 2 | 96.4 | 94.7 | 96.0 | 96.4 | 96.5 | 96.0 | 95.0 | 95.4 |
| 3 | 96.5 | 94.7 | 96.3 | 96.7 | 96.7 | 96.7 | 94.4 | 94.9 |
| 4 | 97.2 | 95.2 | 96.7 | 97.4 | 97.3 | 97.3 | 95.1 | 95.7 |
| 6 | 97.0 | 94.2 | 96.2 | 96.8 | 97.1 | 96.9 | 94.0 | 94.5 |
| 9 | 96.7 | 93.6 | 96.0 | 96.6 | 96.5 | 96.9 | 93.4 | 93.8 |

TABLE 8

% Native mAb1 Remaining (SE-HPLC) After Storage at −20° C.

| Time (months) | Formulation # (see Table 6) | | | | | | | |
| --- | --- | --- | --- | --- | --- | --- | --- | --- |
| | 1 | 2 | 3 | 4 | 5 | 6 | 7 | 8 |
| 0 | 96.4 | 96.2 | 96.4 | 96.5 | 96.5 | 96.6 | 96.2 | 96.5 |
| 1 | 96.7 | 94.5 | 96.0 | 96.8 | 96.5 | 96.3 | 94.1 | 94.5 |
| 2 | 96.4 | 90.9 | 95.3 | 96.4 | 96.4 | 96.4 | 90.9 | 91.8 |
| 3 | 96.9 | 90.1 | 95.1 | 96.6 | 96.6 | 96.7 | 90.5 | 90.9 |
| 4 | 97.2 | 90.7 | 95.8 | 97.4 | 97.1 | 97.1 | 91.4 | 91.8 |
| 6 | 96.9 | 86.9 | 94.1 | 96.9 | 96.9 | 97.1 | 87.5 | 88.5 |
| 9 | 96.5 | 86.0 | 93.3 | 96.6 | 96.6 | 96.7 | 86.7 | 87.5 |

Figure 3:
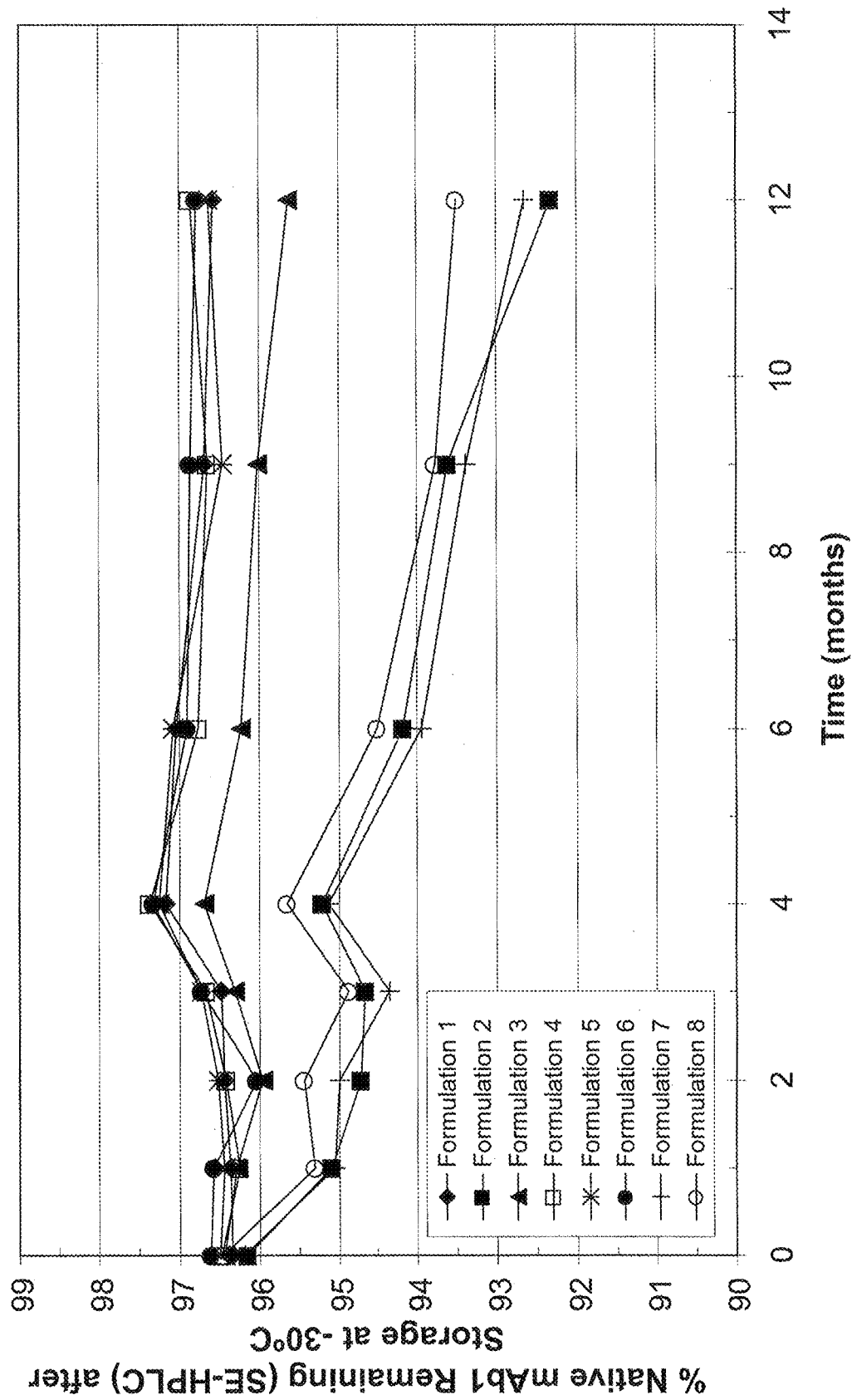
FIG. 3 shows the percent of native mAb1 remaining in various minimal excipient formulations, as measured by SE-HPLC, following various amounts of time of storage at −30° C. Filled diamonds represent formulation 1 (80 mg/mL mAb1, 0.13% polysorbate 20, 6% sucrose, 10 mM histidine); filled squares represent formulation 2 (80 mg/mL mAb1, 0.13% polysorbate 20, 10 mM histidine); filled triangles represent formulation 3 (80 mg/mL mAb, 1% sucrose, 10 mM histidine); open squares represent formulation 4 (80 mg/mL mAb1, 2% sucrose, 10 mM histidine); asterisks represent formulation 5 (80 mg/mL mAb1, 4% sucrose, 10 mM histidine); filled circles represent formulation 6 (80 mg/mL mAb1, 6% sucrose, 10 mM histidine); crosses represent formulation 7 (80 mg/mL antibody, 10 mM histidine); and open circles represent formulation 8 (65 mg/mL antibody, 10 mM histidine). All formulations are set out in Table 6 (see Example 2, below).
Figure 4:
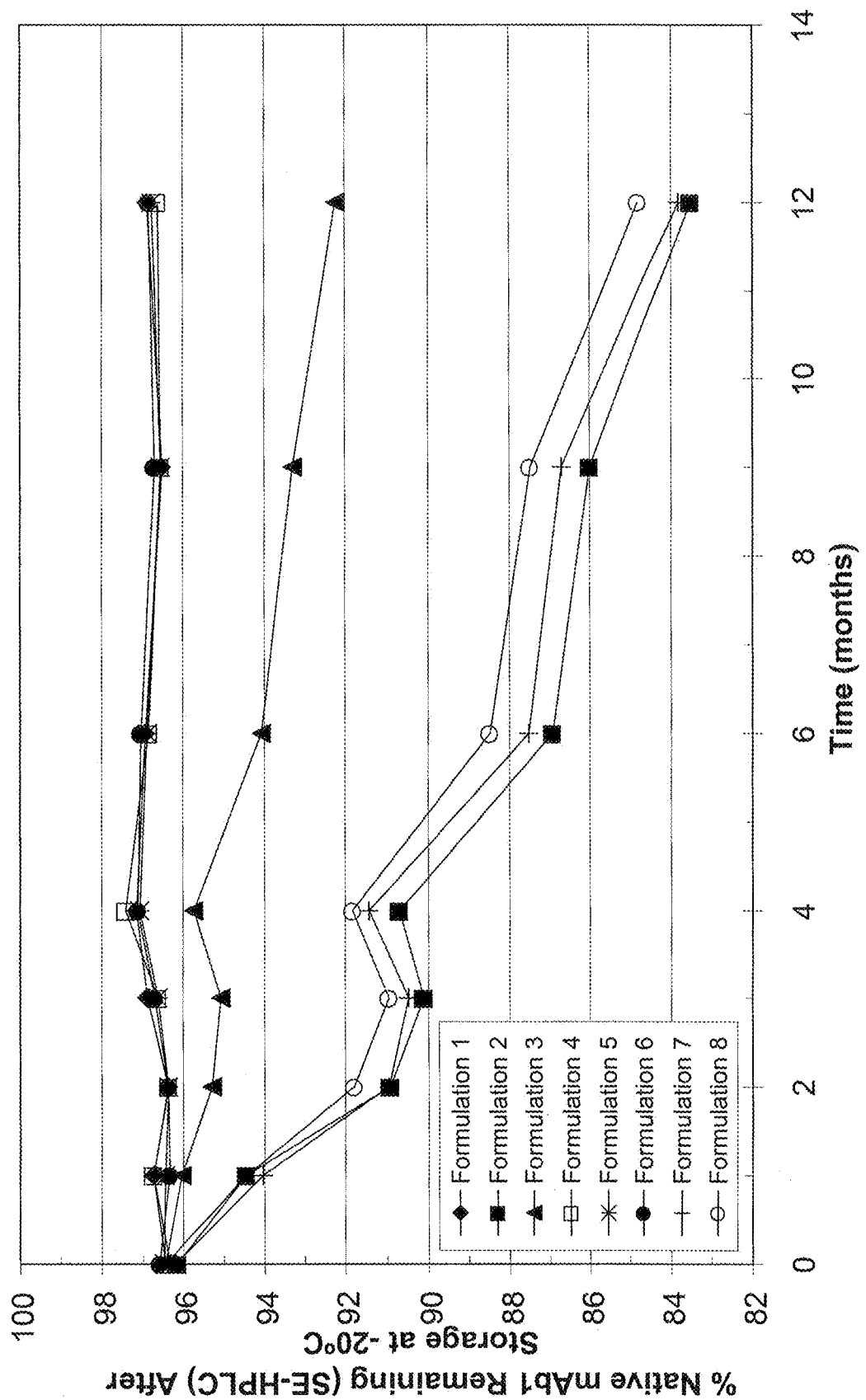
FIG. 4 shows the percent of native mAb1 remaining in various minimal excipient formulations, as measured by SE-HPLC, following various amounts of time of storage at −20° C. Filled diamonds represent formulation 1 (80 mg/mL mAb1, 0.13% polysorbate 20, 6% sucrose, 10 mM histidine); filled squares represent formulation 2 (80 mg/mL mAb1, 0.13% polysorbate 20, 10 mM histidine); filled triangles represent formulation 3 (80 mg/mL mAb, 1% sucrose, 10 mM histidine); open squares represent formulation 4 (80 mg/mL mAb1, 2% sucrose, 10 mM histidine); asterisks represent formulation 5 (80 mg/mL mAb1, 4% sucrose, 10 mM histidine); filled circles represent formulation 6 (80 mg/mL mAb1, 6% sucrose, 10 mM histidine); crosses represent formulation 7 (80 mg/mL antibody, 10 mM histidine); and open circles represent formulation 8 (65 mg/mL antibody, 10 mM histidine). All formulations are set out in Table 6 (see Example 2, below).

The results of Tables 7 and 8 are depicted in FIGS. 3 and 4, respectively. As shown in this Example, the stability of mAb1 was maintained to a significant extent in formulations 1, 4, 5 and 6 after several months of storage at −20° C. and −30° C. These results indicate that the stability of mAb1 at −20° C. and −30° C. can be enhanced by the addition of at least 2% sucrose.

Example 3. Stabilized Formulation of mAb1

A stabilized formulation containing various concentrations of mAb1 was prepared for use in Examples 4 and 5 below. This formulation, designated "Formulation A", is shown in Table 9.

TABLE 9

| Stabilized mAb1 Formulation "A" | |
| --- | --- |
| Component | Formulation A |
| mAb1 | 25-100 mg/mL |
| Histidine | 10 mM |
| Polysorbate 20 | 0.2% |
| Sucrose | 10% | pH adjusted to 6.0

Example 4. Stability of Formulation A after Storage at 5° C.

Formulation A (see Example 3) containing 25, 50 or 100 mg/mL mAb1 was tested for stability after several months of storage at 5° C. in clear vials. Stability was assessed by the following parameters: (a) visual appearance; (b) turbidity (OD 405 nm); (c) pH; (d) percent total mAb1 recovered (as measured by RP-HPLC); (d) percent native mAb1 recovered (as measured by SE-HPLC); (e) percent main peak mAb1 recovered (as measured by CEX-HPLC); and (f) percent acidic species mAb1 recovered (as measured by CEX-HPLC). The stability results for Formulation A containing 25, 50 and 100 mg/mL of mAb1 are summarized in Tables 10, 11 and 12, respectively.

TABLE 10

Stability of Formulation A Containing 25 mg/mL mAb1 After Storage at 5° C. in Clear Vials

| | Length of 5° C. Storage (months) | | | | | | |
| --- | --- | --- | --- | --- | --- | --- | --- |
| Parameter | 0 | 1 | 2 | 3 | 6 | 9 | 12 |
| Visual Appearance | Pass | Pass | Pass | Pass | Pass | Pass | Pass |
| Turbidity (OD 405 nm) | 0.00 | 0.00 | 0.00 | 0.00 | 0.00 | 0.00 | 0.00 |
| pH | 6.0 | 6.1 | 6.1 | 6.1 | 6.1 | 6.1 | 6.1 |
| % Total mAb1 Recovered | 100 | 99 | 101 | 112 | 103 | 94 | 101 |
| % Native mAb1 Recovered | 97.5 | 98.0 | 97.5 | 97.6 | 97.5 | 97.5 | 97.8 |
| % Main Peak mAb1 Recovered | 58.4 | 57.9 | 58.7 | 58.1 | 57.9 | 57.9 | 58.4 |
| % Acidic Species mAb1 Recovered | 26.5 | 28.0 | 26.5 | 28.0 | 27.3 | 28.0 | 27.9 |

TABLE 11A

Stability of Formulation A Containing 50 mg/mL mAb1 After Storage at 5° C. in Clear Vials (0-9 months)

| | Length of 5° C. Storage (months) | | | | | |
| --- | --- | --- | --- | --- | --- | --- |
| Parameter | 0 | 1 | 2 | 3 | 6 | 9 |
| Visual Appearance | Pass | Pass | Pass | Pass | Pass | Pass |
| Turbidity (OD 405 nm) | 0.00 | 0.00 | 0.00 | 0.00 | 0.00 | 0.00 |
| pH | 5.8 | 5.9 | 5.8 | 5.9 | 5.9 | 6.0 |
| % Total mAb1 Recovered | 100 | 99 | 104 | 106 | 100 | 109 |
| % Native mAb1 Recovered | 97.4 | 97.5 | 97.3 | 97.2 | 97.3 | 97.2 |
| % Main Peak mAb1 Recovered | 57.1 | 56.7 | 58.0 | 54.2 | 53.3 | 57.9 |
| % Acidic Species mAb1 Recovered | 27.6 | 26.7 | 27.6 | 28.5 | 26.8 | 26.9 |

TABLE 11B

Stability of Formulation A Containing 50 mg/mL mAb1
After Storage at 5° C. in Clear Vials (12-24 months)

| Parameter | Length of 5° C. Storage (months) | | |
|---|---|---|---|
| | 12 | 18 | 24 |
| Visual Appearance | Pass | Pass | Pass |
| Turbidity (OD 405 nm) | 0.00 | 0.00 | 0.00 |
| pH | 5.9 | 6.0 | 5.9 |
| % Total mAb1 Recovered | 103 | 107 | 105 |
| % Native mAb1 Recovered | 97.1 | 97.1 | 96.9 |
| % Main Peak mAb1 Recovered | 56.4 | 57.1 | 56.4 |
| % Acidic Species mAb1 Recovered | 28.1 | 28.3 | 29.0 |

TABLE 12A

Stability of Formulation A Containing 100 mg/mL mAb1 After
Storage at 5° C. in Clear Vials (0-9 months)

| Parameter | Length of 5° C. Storage (months) | | | | | |
|---|---|---|---|---|---|---|
| | 0 | 1 | 2 | 3 | 6 | 9 |
| Visual Appearance | Pass | Pass | Pass | Pass | Pass | Pass |
| Turbidity (OD 405 nm) | 0.00 | 0.00 | 0.00 | 0.00 | 0.00 | 0.00 |
| pH | 5.9 | 6.0 | 5.9 | 5.9 | 5.9 | 5.9 |
| % Total mAb1 Recovered | 100 | 99 | 100 | 107 | 101 | 106 |
| % Native mAb1 Recovered | 97.3 | 97.0 | 97.0 | 97.1 | 96.9 | 96.9 |
| % Main Peak mAb1 Recovered | 55.1 | 55.5 | 57.9 | 55.9 | 55.4 | 56.8 |
| % Acidic Species mAb1 Recovered | 27.6 | 26.9 | 27.4 | 29.6 | 27.4 | 27.4 |

TABLE 12B

Stability of Formulation A Containing 100 mg/mL mAb1
After Storage at 5° C. in Clear Vials (12-24 months)

| Parameter | Length of 5° C. Storage (months) | | |
|---|---|---|---|
| | 12 | 18 | 24 |
| Visual Appearance | Pass | Pass | Pass |
| Turbidity (OD 405 nm) | 0.00 | 0.00 | 0.00 |
| pH | 6.0 | 6.0 | 6.0 |
| % Total mAb1 Recovered | 101 | 102 | 103 |
| % Native mAb1 Recovered | 96.8 | 96.7 | 96.5 |
| % Main Peak mAb1 Recovered | 57.3 | 57.5 | 56.7 |
| % Acidic Species mAb1 Recovered | 27.3 | 28.1 | 28.7 |

The results of this Example demonstrate that Formulation A containing 25, 50 or 100 mg/mL mAb1 remained stable after at least 9 months of storage, at 5° C. in clear vials, with about 97% or more of native mAb1 remaining in all samples after 9 months of storage under such conditions. For the 50 and 100 mg/mL formulations, 96.9% and 96.5% of native mAb1, respectively, was detected after up to 24 months of storage at 5° C. In addition, the percent acidic species remained at 29% or lower for all time points analyzed, thus confirming the stability of the formulations.

Similar stability studies were also carried out using Formulation A containing 75 mg/mL mAb1 following storage at 2-8° C. No significant degradation was observed for any of the concentrations tested after 24 months of 2-8° C. storage as determined by SE-HPLC and CEX-HPLC (data not shown).

Example 5. Stability of Formulation A Manufactured in Clear and Amber Glass Vials Additional experiments were conducted to compare the stability of Formulation A (see Example 3) containing 25 and 100 mg/mL mAb1 manufactured in amber glass vials to the same formulation manufactured in clear vials. Two types of amber vials were used in this Example: 5 mL and 20 mL amber vials. Stability was assessed following storage at 5° C., 25° C. or 45° C. based on the same parameters as used in Example 4. The results for the 25 mg/mL and 100 mg/mL formulations are summarized in Tables 13 through 21.

TABLE 13

Stability of Formulation A Containing 25 mg/mL
mAb1 After Storage at 5° C. in 5 mL clear Vials

| Parameter | Storage at 5° C. (months) | | | | | | |
|---|---|---|---|---|---|---|---|
| | t = 0 0 | 1 | 2 | 3 | 6 | 9 | 12 |
| Visual Appearance | Pass | Pass | Pass | Pass | Pass | Pass | Pass |
| Turbidity (OD 405 nm) | 0.0 | 0.0 | 0.0 | 0.0 | 0.0 | 0.0 | 0.0 |
| pH | 6.0 | 6.0 | 6.0 | 6.0 | 6.0 | 6.0 | 6.1 |
| % Total mAb1 Recovered | 100 | 106 | 103 | 98 | 100 | 100 | 101 |
| % Native mAb1 Recovered | 97.1 | 97.0 | 96.9 | 96.9 | 97.0 | 96.4 | 96.6 |
| % Main Peak mAb1 Recovered | 57.8 | 56.8 | 56.2 | 54.2 | 56.4 | 56.4 | 56.8 |
| % Acidic Species mAb1 Recovered | 27.9 | 30.7 | 30.8 | 33.0 | 30.6 | 29.8 | 30.1 |

TABLE 14

Stability of Formulation A Containing 100 mg/mL
mAb1 After Storage at 5° C. in 5 mL Clear Vials

| Parameter | Storage at 5° C. (months) | | | | | | |
|---|---|---|---|---|---|---|---|
| | t = 0 0 | 1 | 2 | 3 | 6 | 9 | 12 |
| Visual Appearance | Pass | Pass | Pass | Pass | Pass | Pass | Pass |
| Turbidity (OD 405 nm) | 0.0 | 0.0 | 0.0 | 0.0 | 0.0 | 0.0 | 0.0 |
| pH | 6.0 | 6.1 | 6.0 | 6.1 | 6.0 | 6.1 | 6.1 |
| % Total mAb1 Recovered | 100 | 106 | 104 | 97 | 100 | 99 | 100 |
| % Native mAb1 Recovered | 96.2 | 96.3 | 96.1 | 96.0 | 95.9 | 95.5 | 95.4 |
| % Main Peak mAb1 Recovered | 57.6 | 57.3 | 57.9 | 55.5 | 56.2 | 56.4 | 55.4 |
| % Acidic Species mAb1 Recovered | 28.2 | 30.2 | 29.4 | 31.1 | 30.7 | 30.0 | 32.2 |

TABLE 15

Stability of Formulation A Containing 25 mg/mL mAb1 After Storage at 5° C. in 5 mL Amber Vials

| | | Storage at 5° C. (months) | | | | | |
|---|---|---|---|---|---|---|---|
| Parameter | t = 0<br>0 | 1 | 2 | 3 | 6 | 9 | 12 |
| Visual Appearance | Pass | Pass | Pass | Pass | Pass | Pass | Pass |
| Turbidity (OD 405 nm) | 0.0 | 0.0 | 0.0 | 0.0 | 0.0 | 0.0 | 0.0 |
| pH | 6.0 | 6.0 | 6.0 | 6.0 | 6.0 | 6.0 | 6.0 |
| % Total mAb1 Recovered | 100 | 104 | 104 | 98 | 99 | 97 | 101 |
| % Native mAb1 Recovered | 97.1 | 97.4 | 96.8 | 96.7 | 96.7 | 96.1 | 96.3 |
| % Main Peak mAb1 Recovered | 57.8 | 56.4 | 56.3 | 56.1 | 55.7 | 55.9 | 55.2 |
| % Acidic Species mAb1 Recovered | 27.9 | 30.4 | 30.6 | 31.8 | 31.0 | 30.5 | 32.9 |

TABLE 16

Stability of Formulation A Containing 100 mg/mL mAb1 After Storage at 5° C. in 5 mL Amber Vials

| | | Storage at 5° C. (months) | | | | | |
|---|---|---|---|---|---|---|---|
| Parameter | t = 0<br>0 | 1 | 2 | 3 | 6 | 9 | 12 |
| Visual Appearance | Pass | Pass | Pass | Pass | Pass | Pass | Pass |
| Turbidity (OD 405 nm) | 0.0 | 0.0 | 0.0 | 0.0 | 0.0 | 0.0 | 0.0 |
| pH | 6.0 | 6.0 | 6.0 | 6.0 | 6.0 | 6.0 | 6.1 |
| % Total mAb1 Recovered | 100 | 102 | 104 | 97 | 101 | 100 | 100 |
| % Native mAb1 Recovered | 96.2 | 95.0 | 96.0 | 96.0 | 95.8 | 95.0 | 95.3 |
| % Main Peak mAb1 Recovered | 57.6 | 56.9 | 58.0 | 55.6 | 56.3 | 56.5 | 55.1 |
| % Acidic Species mAb1 Recovered | 28.2 | 30.1 | 29.4 | 31.4 | 30.4 | 30.0 | 32.3 |

TABLE 17

Stability of Formulation A Containing 25 mg/mL mAb1 After Storage at 5° C. in 20 mL Amber Vials

| | | Storage at 5° C. (months) | | | | | |
|---|---|---|---|---|---|---|---|
| Parameter | t = 0<br>0 | 1 | 2 | 3 | 6 | 9 | 12 |
| Visual Appearance | Pass | Pass | Pass | Pass | Pass | Pass | Pass |
| Turbidity (OD 405 nm) | 0.0 | 0.0 | 0.0 | 0.0 | 0.0 | 0.0 | 0.0 |
| pH | 6.0 | 6.0 | 6.0 | 6.0 | 6.0 | 6.0 | 6.0 |
| % Total mAb1 Recovered | 100 | 105 | 103 | 97 | 101 | 98 | 101 |
| % Native mAb1 Recovered | 97.1 | 96.9 | 97.0 | 96.8 | 97.0 | 96.2 | 96.6 |
| % Main Peak mAb1 Recovered | 57.8 | 56.4 | 57.1 | 55.9 | 55.6 | 56.1 | 55.2 |
| % Acidic Species mAb1 Recovered | 27.9 | 20.9 | 30.2 | 30.5 | 30.7 | 30.0 | 31.9 |

TABLE 18

Stability of Formulation A Containing 100 mg/mL mAb1 After Storage at 5° C. in 20 mL Amber Vials

| | | Storage at 5° C. (months) | | | | | |
|---|---|---|---|---|---|---|---|
| Parameter | t = 0<br>0 | 1 | 2 | 3 | 6 | 9 | 12 |
| Visual Appearance | Pass | Pass | Pass | Pass | Pass | Pass | Pass |
| Turbidity (OD 405 nm) | 0.0 | 0.0 | 0.0 | 0.0 | 0.0 | 0.0 | 0.0 |
| pH | 6.0 | 6.0 | 6.0 | 6.0 | 6.0 | 6.0 | 6.0 |
| % Total mAb1 Recovered | 100 | 105 | 103 | 97 | 99 | 98 | 100 |
| % Native mAb1 Recovered | 96.2 | 96.2 | 96.0 | 96.0 | 95.8 | 95.4 | 95.5 |
| % Main Peak mAb1 Recovered | 57.6 | 57.9 | 56.3 | 56.5 | 56.5 | 56.4 | 55.3 |
| % Acidic Species mAb1 Recovered | 28.2 | 29.8 | 30.4 | 30.3 | 30.6 | 30.0 | 30.9 |

TABLE 19

Stability of Formulation A Containing 100 mg/mL mAb1 After Storage at 25° C. and 45° C. in Clear Vials

| | t = 0 | Storage at 45° C. (days) | | | Storage at 25° C. (months) | | | |
|---|---|---|---|---|---|---|---|---|
| Parameter | 0 | 7 | 14 | 28 | 1 | 2 | 3 | 6 |
| Visual Appearance | Pass | Pass | Pass | Pass | Pass | Pass | Pass | Pass |
| Turbidity (OD 405 nm) | 0.0 | 0.0 | 0.0 | 0.0 | 0.0 | 0.0 | 0.0 | 0.0 |
| pH | 6.0 | 6.1 | 6.1 | 6.1 | 6.1 | 6.1 | 6.1 | 6.1 |
| % Total mAb1 Recovered | 100 | 101 | 97 | 105 | 105 | 102 | 97 | 101 |
| % Native mAb1 Recovered | 95.6 | 94.8 | 93.8 | 91.2 | 94.6 | 93.7 | 93.1 | 93.4 |
| % Main Peak mAb1 Recovered | 57.6 | 45.7 | 34.9 | 22.3 | 53.1 | 49.0 | 43.0 | 37.9 |
| % Acidic Species mAb1 Recovered | 28.2 | 37.3 | 49.8 | 70.8 | 32.5 | 36.8 | 42.4 | 53.8 |

TABLE 20

Stability of Formulation A Containing 100 mg/mL mAb1 After Storage at 25° C. and 45° C. in 5 mL Amber Vials

| Parameter | t = 0 | Storage at 45° C. (days) | | | Storage at 25° C. (months) | | | |
|---|---|---|---|---|---|---|---|---|
| | 0 | 7 | 14 | 28 | 1 | 2 | 3 | 6 |
| Visual Appearance | Pass | Pass | Pass | Pass | Pass | Pass | Pass | Pass |
| Turbidity (OD 405 nm) | 0.00 | 0.00 | 0.01 | 0.02 | 0.00 | 0.00 | 0.01 | 0.02 |
| pH | 6.0 | 6.1 | 6.1 | 6.1 | 6.1 | 6.1 | 6.1 | 6.0 |
| % Total mAb1 Recovered | 100 | 101 | 100 | 105 | 106 | 103 | 97 | 100 |
| % Native mAb1 Recovered | 95.6 | 94.6 | 93.6 | 90.9 | 94.5 | 93.7 | 93.4 | 92.7 |
| % Main Peak mAb1 Recovered | 57.6 | 46.1 | 35.2 | 21.6 | 52.7 | 46.3 | 42.0 | 34.2 |
| % Acidic Species mAb1 Recovered | 28.2 | 37.3 | 50.1 | 70.9 | 32.8 | 39.6 | 43.4 | 57.3 |

TABLE 21

Stability of Formulation A Containing 100 mg/mL mAb1 After Storage at 25° C. and 45° C. in 20 mL Amber Vials

| Parameter | t = 0 | Storage at 45° C. (days) | | | Storage at 25° C. (months) | | | |
|---|---|---|---|---|---|---|---|---|
| | 0 | 7 | 14 | 28 | 1 | 2 | 3 | 6 |
| Visual Appearance | Pass | Pass | Pass | Pass | Pass | Pass | Pass | Pass |
| Turbidity (OD 405 nm) | 0.00 | 0.01 | 0.00 | 0.02 | 0.00 | 0.01 | 0.00 | 0.02 |
| pH | 6.0 | 6.0 | 6.1 | 6.1 | 6.0 | 6.0 | 6.0 | 6.0 |
| % Total mAb1 Recovered | 100 | 101 | 101 | 105 | 104 | 103 | 96 | 100 |
| % Native mAb1 Recovered | 95.6 | 94.9 | 93.8 | 91.5 | 94.3 | 94.0 | 93.6 | 93.5 |
| % Main Peak mAb1 Recovered | 57.6 | 45.7 | 34.2 | 23.3 | 52.7 | 49.3 | 43.5 | 36.7 |
| % Acidic Species mAb1 Recovered | 28.2 | 36.7 | 51.1 | 68.6 | 32.5 | 35.8 | 41.3 | 55.0 |

As shown in this Example, Formulation A containing 25 mg/mL or 100 mg/mL mAb1 exhibited equivalent stability profiles when stored in either clear or amber vials. Moreover, as demonstrated in Example 4 for storage in clear vials, relatively high stability of mAb1 was maintained in Formulation A when stored in either clear or amber vials at 5° C. for up to 12 months.

Example 6. Effect of Arginine, Histidine and Sucrose Concentrations on Viscosity and Stability of Formulations Containing 150 mg/mL mAb1

Several formulations were prepared containing 150 mg/mL, 175 mg/mL and 200 mg/mL mAb1 and various quantities of histidine, arginine and sucrose. Viscosity and osmolality were measured for each formulation. Additionally, the stability of the 150 mg/mL formulations after 4 weeks of storage at 45° C. was assessed in terms of percent native mAb1 remaining (by SE-HPLC) and percent main peak remaining (by CEX-HPLC). The results are summarized in Table 22.

The results presented in Table 16 indicate that increasing the histidine concentration to 25 mM or 100 mM and adding arginine to the formulation (25 mM or 50 mM) significantly reduced the viscosity of the formulation as compared to formulations containing only 10 mM histidine and no arginine. Furthermore, reducing the sucrose concentration from 10% to 5% with the added histidine and arginine decreased the viscosity of the formulation to an even greater extent.

Based at least in part on the foregoing, the following Formulations (designated "Formulation B" and "Formulation C") set forth in Table 23 were prepared.

TABLE 22

Effect of Arginine, Histidine and Sucrose on Viscosity and Stability of mAb1 Formulations

| mAb1 (mg/mL) | [Histidine] (mM) | [Arginine] (mM) | [Sucrose] (%) | Viscosity (cPoise) | Osmolality (mOsm) | % native mAb1 remaining* | % acidic species |
|---|---|---|---|---|---|---|---|
| 150 | 10 | 0 | 10 | ~15 | 375 | 90.8 | 19.9 |
| 150 | 25 | 25 | 10 | ~11.5 | 500 | 91.6 | 19.5 |
| 150 | 25 | 25 | 5 | ~8.5 | 305 | 91.8 | 19.8 |
| 150 | 25 | 25 | 2.5 | ~8.0 | 220 | 91.1 | 19.9 |
| 150 | 25 | 25 | 0 | ~8.5 | 115 | 90.3 | 20.6 |
| 175 | 10 | 0 | 10 | ~27 | 395 | | |
| 175 | 25 | 25 | 10 | ~20.5 | 415 | | |
| 175 | 25 | 25 | 5 | ~19 | 300 | | |
| 175 | 25 | 50 | 5 | ~14.5 | 390 | | |
| 175 | 100 | 0 | 5 | ~12.5 | 415 | | |
| 175 | 100 | 50 | 5 | ~10 | 515 | | |
| 200 | 10 | 0 | 10 | ~44 | 410 | | |
| 200 | 25 | 25 | 10 | ~35 | 480 | | |
| 200 | 25 | 25 | 5 | ~30 | 300 | | |
| 200 | 25 | 25 | 0 | ~28 | 130 | | |
| 200 | 100 | 0 | 10 | ~27 | 570 | | |
| 200 | 100 | 50 | 10 | ~21 | 670 | | |

Initial % native mAb1 = 96.5% (SE-HPLC)

TABLE 23

Stabilized mAb1 Formulations "B" and "C"

| Component | Formulation B | Formulation C |
|---|---|---|
| mAb1 | 25-200 mg/mL | 25-200 mg/mL |
| Histidine | 25 mM | 25 mM |
| Polysorbate 20 | 0.2% | 0.2% |
| Sucrose | 5% | 5% |
| Arginine | 25 mM | 50 mM | pH adjusted to 6.0

Example 7. Stability of Formulation B Containing 150 mg/mL mAb1 when Manufactured in a Vial and Syringes Formulation B (see Table 23) containing 150 mg/mL mAb1 was prepared in a 2 mL glass vial and in two different syringes: regular and low tungsten. The preparations were stored at 5, 25 and 45° C. for various amounts of time. The stability of mAb1 following storage was measured by SE-HPLC and CEX-HPLC. The results are shown in Table 24. (An increase in percent acidic species is consistent with deamidation of the antibody and is thus considered an undesired phenomenon with respect to the pharmaceutical formulations of the present invention).

TABLE 24

Stability of Formulation B Containing 150 mg/mL mAb1 in Vial and Syringe

| | | 2 mL Glass Vial | | Regular Syringe | | Low Tungsten Syringe | |
|---|---|---|---|---|---|---|---|
| Temp | Time | % Native (SE-HPLC) | % Acidic (CEX-HPLC) | % Native (SE-HPLC) | % Acidic (CEX-HPLC) | % Native (SE-HPLC) | % Acidic (CEX-HPLC) |
| — | Start | 96.7 | 32.2 | 96.5 | 32.3 | 96.7 | 31.7 |
| 45° C. | 14 days | 94.1 | 52.7 | 94.3 | 54.5 | 94.3 | 56.1 |
| 45° C. | 28 days | 92.7 | 69.7 | 92.7 | 69.7 | 92.5 | 70.8 |
| 45° C. | 56 days | 86.7 | 84.7 | 87.8 | 82.6 | 86.9 | 83.5 |
| 25° C. | 1 month | 95.1 | 31.2 | 95.7 | 30.6 | 95.6 | 31.1 |
| 25° C. | 2 month | 95.3 | 34.6 | 94.7 | 37.4 | 96.0 | 36.3 |
| 25° C. | 3 month | 94.3 | 40.6 | 93.9 | 43.7 | 94.1 | 42.6 |
| 5° C. | 1 month | 96.2 | 30.2 | 96.5 | 29.1 | 96.4 | 29.3 |
| 5° C. | 2 month | 96.3 | 29.3 | 96.4 | 29.0 | 96.4 | 29.1 |
| 5° C. | 3 month | 95.7 | 29.4 | 95.8 | 29.6 | 95.8 | 29.6 |

As shown in this table, Formulation B containing 150 mg/mL mAb1, stored at 5° C. in a glass vial or syringe, remained relatively stable for at least 3 months.

Example 8: Stability of mAb1 Formulations in Prefilled Syringes

A series of experiments was carried out to assess the stability of different mAb1 formulations in prefilled syringes. For these experiments various luer and staked needle, regular-tungsten and low-tungsten syringes were used in combination with different types of plungers (coated and uncoated) and tip-caps. The formulations were tested for stability after storage in prefilled syringes at 45° C., 25° C. and 5° C. for various amounts of time (ranging from 14 days to 12 months, depending on the conditions tested).

Six different formulations of mAb1 were tested for stability in prefilled syringes in this Example: (1) Formulation A (see Table 9) containing 100 mg/mL mAb1; (2) Formulation A (see Table 9) containing 25 mg/mL mAb1; (3) Formulation B (see Table 23) containing 150 mg/mL mAb1; (4) Formulation B (see Table 23) containing 25 mg/mL mAb1; (5) Formulation C (see Table 23) containing 175 mg/mL of mAb1; and (6) Formulation C (see Table 23) containing 25 mg/mL of mAb1.

Stability was assessed by the following parameters: (a) visual analysis; (b) turbidity ($OD_{405\ nm}$); (c) percent recovery by RP-HPLC; (d) percent native mAb1 by SE-HPLC; (e) percent main peak mAb1 by CEX-HPLC; and (f) percent acidic species by CEX-HPLC.

The results from a representative experiment assessing the stability of Formulation A, containing 100 mg/mL mAb1 in two different syringes (Syringe #1 and Syringe #2) are shown in Tables 25 and 26 below.

TABLE 25

Stability of Formulation A containing 100 mg/mL mAb1 in Staked Needle Prefilled Syringe #1

| Syringe #1 Description: | |
|---|---|
| Syringe: | BD 1 mL long 29 ga x ½" Physiolis, Low Tungsten |
| Plunger: | West FluroTec ® 4023/50 |
| Tip Cap: | BD 260 |
| Siliconization: | Sprayed |

| Temp | Time | Visual Analysis | Turbidity ($OD_{405\ nm}$) | % Recovery | % Native mAb1 | % Main Peak | % Acidic Species |
|---|---|---|---|---|---|---|---|
| — | Start | Pass | 0.00 | 100 | 96.6 | 56.9 | 28.7 |
| 45° C. | 14 days | Pass | 0.00 | 99 | 95.1 | 32.7 | 50.7 |
| 45° C. | 28 days | Pass | 0.01 | 103 | 92.6 | 20.9 | 66.1 |
| 45° C. | 56 days | Pass | 0.03 | 105 | 88.8 | 9.9 | 80.9 |
| 25° C. | 1 month | Pass | 0.00 | 106 | 95.6 | 52.4 | 32.0 |
| 25° C. | 2 months | Pass | 0.00 | 107 | 95.2 | 48.0 | 37.0 |
| 25° C. | 3 months | Pass | 0.00 | 106 | 94.2 | 44.8 | 41.8 |
| 25° C. | 6 months | Pass | 0.01 | 101 | 93.7 | 34.8 | 53.9 |
| 25° C. | 9 months | Pass | 0.03 | 98 | 91.4 | 26.1 | 64.6 |
| 25° C. | 12 months | Pass | 0.03 | 101 | 89.9 | 21.3 | 69.4 |
| 5° C. | 1 month | Pass | 0.00 | 110 | 96.4 | 56.8 | 29.9 |
| 5° C. | 2 months | Pass | 0.00 | 108 | 96.2 | 55.7 | 31.1 |
| 5° C. | 3 months | Pass | 0.00 | 104 | 96.0 | 56.3 | 30.0 |
| 5° C. | 6 months | Pass | 0.00 | 100 | 96.5 | 55.0 | 31.3 |
| 5° C. | 9 months | Pass | 0.00 | 98 | 96.2 | 56.7 | 30.3 |
| 5° C. | 12 months | Pass | 0.00 | 101 | 95.4 | 57.3 | 30.2 |

The results from another representative experiment assessing the stability of Formulation C, containing 175 mg/mL mAb1 in two different syringes (Syringe #1 and Syringe #3) are shown in Tables 27 and 28 below.

TABLE 26

Stability of Formulation A containing 100 mg/mL mAb1 in Staked Needle Prefilled Syringe #2

| Syringe #2 Description: | |
|---|---|
| Syringe: | Schott 1 mL Long SN CF 29 ga x ½" |
| Plunger: | West FluroTec ® 4023/50 |
| Tip Cap: | Stelmi 4800 w/RNS |
| Siliconization: | Sprayed |

| Temp | Time | Visual Analysis | Turbidity ($OD_{405\ nm}$) | % Recovery | % Native mAb1 | % Main Peak | % Acidic Species |
|---|---|---|---|---|---|---|---|
| — | Start | Pass | 0.00 | 100 | 96.3 | 57.5 | 28.0 |
| 45° C. | 14 days | Pass | 0.00 | 100 | 95.2 | 33.7 | 49.6 |
| 45° C. | 28 days | Pass | 0.00 | 103 | 93.3 | 22.8 | 64.7 |
| 45° C. | 56 days | Pass | 0.03 | 107 | 88.0 | 9.9 | 81.1 |
| 25° C. | 1 month | Pass | 0.00 | 108 | 95.5 | 52.5 | 31.8 |
| 25° C. | 2 months | Pass | 0.00 | 107 | 95.2 | 49.2 | 35.7 |
| 25° C. | 3 months | Fail | 0.00 | 106 | 93.9 | 43.1 | 42.0 |
| 25° C. | 6 months | Fail | 0.00 | 102 | 92.9 | 34.4 | 54.0 |
| 25° C. | 9 months | Pass | 0.02 | 100 | 92.3 | 26.9 | 63.5 |
| 25° C. | 12 months | Pass | 0.03 | 103 | 90.0 | 20.0 | 70.2 |
| 5° C. | 1 month | Pass | 0.00 | 111 | 96.3 | 56.7 | 29.9 |
| 5° C. | 2 months | Pass | 0.00 | 112 | 95.6 | 55.9 | 31.1 |
| 5° C. | 3 months | Pass | 0.00 | 106 | 96.1 | 57.2 | 29.4 |
| 5° C. | 6 months | Pass | 0.00 | 102 | 96.0 | 54.9 | 31.6 |

TABLE 26-continued

Stability of Formulation A containing 100 mg/mL mAb1 in Staked Needle Prefilled Syringe #2

| | | | | | | | |
|---|---|---|---|---|---|---|---|
| 5° C. | 9 months | Pass | 0.00 | 100 | 95.9 | 56.7 | 30.2 |
| 5° C. | 12 months | Pass | 0.00 | 102 | 95.4 | 56.0 | 30.7 |

TABLE 27

Stability of Formulation C containing 175 mg/mL mAb1 in Staked Needle Prefilled Syringe #1

Syringe #1 Description:

| | |
|---|---|
| Syringe: | BD 1 mL long 29 ga × ½" Physiolis, Low Tungsten |
| Plunger: | West FluroTec ® 4023/50 |
| Tip Cap: | BD 260 |
| Siliconization: | Sprayed |

| Temp | Time | Visual Analysis | Turbidity (OD$_{405\ nm}$) | % Recovery | % Native mAb1 | % Main Peak | % Acidic Species |
|---|---|---|---|---|---|---|---|
| — | Start | Pass | 0.00 | 100 | 96.7 | 59.7 | 32.4 |
| 45° C. | 7 days | Pass | 0.01 | 102 | 96.1 | 48.6 | 39.5 |
| 45° C. | 14 days | Pass | 0.03 | 97 | 95.0 | 36.9 | 50.0 |
| 45° C. | 28 days | Pass | 0.03 | 98 | 91.9 | 24.7 | 66.0 |
| 45° C. | 56 days | Pass | 0.05 | 97 | 91.9 | 12.3 | 83.3 |
| 25° C. | 1 month | Pass | 0.02 | 99 | 95.4 | 56.9 | 33.8 |
| 25° C. | 2 months | Pass | 0.00 | 100 | 95.0 | 51.1 | 39.8 |
| 5° C. | 1 month | Pass | 0.00 | 98 | 96.1 | 59.5 | 32.7 |
| 5° C. | 2 months | Pass | 0.00 | 101 | 96.4 | 56.3 | 37.1 |

TABLE 28

Stability of Formulation C containing 175 mg/mL mAb1 in Staked Needle Prefilled Syringe #3

Syringe #1 Description:

| | |
|---|---|
| Syringe: | Daikyo Seiko CZ 1 mL std 30 ga × ½" |
| Plunger: | Daikyo D-21-6-1 FluroTec ® Coated |
| Tip Cap: | 7028 |
| Siliconization: | N/A |

| Temp | Time | Visual Analysis | Turbidity (OD$_{405\ nm}$) | % Recovery | % Native mAb1 | % Main Peak | % Acidic Species |
|---|---|---|---|---|---|---|---|
| — | Start | Pass | 0.00 | 100 | 96.4 | 58.2 | 33.6 |
| 45° C. | 7 days | Pass | 0.00 | 101 | 95.7 | 45.4 | 40.4 |
| 45° C. | 14 days | Pass | 0.01 | 101 | 94.8 | 37.5 | 48.8 |
| 45° C. | 28 days | Pass | 0.04 | 96 | 94.0 | 29.4 | 59.4 |
| 45° C. | 56 days | Pass | 0.06 | 99 | 85.9 | 7.8 | 87.0 |
| 25° C. | 1 month | N/D | N/D | N/D | N/D | N/D | N/D |
| 5° C. | 1 month | Pass | 0.00 | 100 | 96.4 | 56.7 | 34.0 |
| 5° C. | 2 months | Pass | 0.00 | 101 | 96.2 | 54.7 | 34.0 |

The results from this set of experiments demonstrate that the different formulations remain relatively stable in prefilled syringes, especially when stored at temperatures of 25° C. and below, for one month or greater. Moreover, the various formulations of the invention appeared to have enhanced stability when contained in low tungsten syringes containing fluorocarbon-coated plungers.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

What is claimed is:

1. A prefilled syringe containing a stable pharmaceutical formulation comprising:
   (i) a human antibody that specifically binds to human interleukin-6 receptor (hIL-6R), wherein the antibody is at a concentration of from about 5 mg/ml to about 200 mg/ml and comprises a heavy chain variable region having the amino acid sequence of SEQ ID NO:18 and a light chain variable region having the amino acid sequence of SEQ ID NO:26;
   (ii) histidine at a concentration of from about 10 mM to about 25 mM;
   (iii) arginine at a concentration of from about 25 mM to about 50 mM;
   (iv) sucrose in an amount of from about 5% to about 10% w/v; and
   (v) polysorbate in an amount of from about 0.1% to about 0.2% w/v,
   wherein the formulation has a pH of about 5.8, about 6.0, or about 6.2, and at least 90% of the native form of the antibody is recovered after 1 month of storage at 45° C., as determined by size exclusion chromatography.

2. The prefilled syringe of claim 1, wherein the histidine is at a concentration of 21 mM.

3. The prefilled syringe of claim 2, wherein the arginine is present at a concentration of 45 mM.

4. The prefilled syringe of claim 3, wherein the sucrose is present in an amount of 5% w/v.

5. The prefilled syringe of claim 4, wherein the polysorbate is present at a concentration of 0.2% w/v.

6. The prefilled syringe of claim 5, wherein the polysorbate is polysorbate 20.

7. The prefilled syringe of claim 6, wherein the formulation has a pH of 6.

8. The prefilled syringe of claim 1, wherein the antibody is at a concentration of from 25 mg/ml to 200 mg/ml.

9. The prefilled syringe of claim 1, wherein the antibody is at a concentration of from 50 mg/ml to 180 mg/ml.

10. The prefilled syringe of claim 9, wherein the antibody is at a concentration of 150 mg/ml.

11. The prefilled syringe of claim 9, wherein the antibody is at a concentration of 175 mg/ml.

12. The prefilled syringe of claim 11, wherein at least 90% of the native form of the antibody is recovered after nine months of storage at 5° C., as determined by size exclusion-high performance liquid chromatography (SE-HPLC).

13. The prefilled syringe of claim 12, wherein at least 95% of the native form of the antibody is recovered after nine months of storage at 5° C., as determined by size exclusion-high performance liquid chromatography (SE-HPLC).

14. The prefilled syringe of claim 13, wherein at least 96% of the native form of the antibody is recovered after nine months of storage at 5° C., as determined by size exclusion-high performance liquid chromatography (SE-HPLC).

15. The prefilled syringe of claim 11, wherein the formulation exhibits a viscosity of less than about 15 cPoise.

16. The prefilled syringe of claim 11, wherein the formulation exhibits a viscosity of less than about 12 cPoise.

17. The prefilled syringe of claim 11, wherein the formulation exhibits a viscosity of less than about 9 cPoise.

18. The prefilled syringe of claim 1 that comprises a fluorocarbon-coated plunger.

19. The prefilled syringe of claim 1 that is a low tungsten syringe.

20. The prefilled syringe of claim 1 that is a staked needle prefilled syringe.

21. The prefilled syringe of claim 1, wherein the prefilled syringe is for use in an autoinjector delivery device.

22. The prefilled syringe of claim 1, wherein the human antibody that specifically binds to hIL-6R consists of two heavy chains and two light chains, each heavy chain comprising the heavy chain variable region comprising the amino acid sequence of SEQ ID NO: 18 and a heavy chain constant region, and each light chain comprising the light chain variable region comprising the amino acid sequence of SEQ ID NO: 26 and a light chain constant region.

23. The prefilled syringe of claim 1, wherein the human antibody that specifically binds to hIL-6R comprises two heavy chains and two light chains, each heavy chain comprising the heavy chain variable region comprising the amino acid sequence of SEQ ID NO: 18 and a heavy chain constant region, and each light chain comprising the light chain variable region comprising the amino acid sequence of SEQ ID NO: 26 and a light chain constant region.

24. A prefilled syringe containing a stable pharmaceutical formulation comprising:
(i) 25 to 200 mg/mL of a human antibody that specifically binds to human interleukin-6 receptor (hIL-6R), wherein the antibody comprises a heavy chain variable region having the amino acid sequence of SEQ ID NO:18 and a light chain variable region having the amino acid sequence of SEQ ID NO:26;
(ii) about 21, 22, 23, 24 or 25 mM histidine;
(iii) about 3%, 4% or 5% w/v sucrose;
(iv) about 0.18%, 0.19% or 0.2% w/v polysorbate 20; and
(v) about 45 or 50 mM arginine,
wherein the formulation has a pH of about 6, and at least 90% of the native form of the antibody is recovered after 1 month of storage at 45° C., as determined by size exclusion chromatography.

25. A prefilled syringe containing a stable pharmaceutical formulation comprising:
(i) about 150 mg/mL of a human antibody that specifically binds to human interleukin-6 receptor (hIL-6R), wherein said antibody comprises a heavy chain and light chain variable region (HCVR/LCVR) amino acid sequence pair of SEQ ID NOs:18/26;
(ii) about 21 mM histidine;
(iii) about 5% sucrose;
(iv) about 0.2% polysorbate 20; and
(v) about 45 mM arginine,
wherein the formulation has a pH of about 6, and at least 90% of the native form of the antibody is recovered after 1 month of storage at 45° C., as determined by size exclusion chromatography.

26. A prefilled syringe containing a stable pharmaceutical formulation comprising:
(i) about 175 mg/mL of a human antibody that specifically binds to human interleukin-6 receptor (hIL-6R), wherein said antibody comprises a heavy chain and light chain variable region (HCVR/LCVR) amino acid sequence pair of SEQ ID NOs:18/26;
(ii) about 21 mM histidine;
(iii) about 5% sucrose;
(iv) about 0.2% polysorbate 20; and
(v) about 45 mM arginine,
wherein the formulation has a pH of about 6, and at least 90% of the native form of the antibody is recovered after 1 month of storage at 45° C., as determined by size exclusion chromatography.

27. The prefilled syringe of claim 1, wherein the prefilled syringe is for use in a reusable or disposable pen delivery device.

* * * * *

SEQUENCE LISTING

<160> NUMBER OF SEQ ID NOS: 74

<210> SEQ ID NO 1
<211> LENGTH: 379
<212> TYPE: DNA
<213> ORGANISM: Artificial Sequence
<220> FEATURE:
<223> OTHER INFORMATION: Synthetic

<400> SEQUENCE: 1

```
gaagtgcagc tggtggagtc tgggggaaac ttggtacagc ctggcaggtc cctgagactc    60
tcctgtgcag cctctggatt catctttgat gattatgcca tgcactgggt ccggcaagct   120
ccagggaagg gcctggagtg ggtctcaggt attagttgga atagtggtag cataggctat   180
gcggactctg tgaagggccg attcaccatc tccagagaca cgccaagaa ctccctgtat    240
ctgcaaatga acagtctgag agctgaggac acggccttgt attactgtgc aaaagatgga   300
ggcagcagct ggttaccgtt cgtctactac tacggtatgg acgtctgggg ccaagggacc   360
acggtcaccg tctcgtcag                                                379
```

<210> SEQ ID NO 2
<211> LENGTH: 126
<212> TYPE: PRT
<213> ORGANISM: Artificial Sequence
<220> FEATURE:
<223> OTHER INFORMATION: Synthetic

<400> SEQUENCE: 2

```
Glu Val Gln Leu Val Glu Ser Gly Gly Asn Leu Val Gln Pro Gly Arg
1               5                   10                  15

Ser Leu Arg Leu Ser Cys Ala Ala Ser Gly Phe Ile Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Gly Gly Ser Ser Trp Leu Pro Phe Val Tyr Tyr Tyr Gly
            100                 105                 110

Met Asp Val Trp Gly Gln Gly Thr Thr Val Thr Val Ser Ser
        115                 120                 125
```

<210> SEQ ID NO 3
<211> LENGTH: 24
<212> TYPE: DNA
<213> ORGANISM: Artificial Sequence
<220> FEATURE:
<223> OTHER INFORMATION: Synthetic

<400> SEQUENCE: 3

```
ggattcatct ttgatgatta tgcc                                           24
```

<210> SEQ ID NO 4
<211> LENGTH: 8
<212> TYPE: PRT
<213> ORGANISM: Artificial Sequence
<220> FEATURE:
<223> OTHER INFORMATION: Synthetic

<400> SEQUENCE: 4

```
Gly Phe Ile Phe Asp Asp Tyr Ala
1               5
```

<210> SEQ ID NO 5
<211> LENGTH: 24
<212> TYPE: DNA
<213> ORGANISM: Artificial Sequence
<220> FEATURE:
<223> OTHER INFORMATION: Synthetic

<400> SEQUENCE: 5
attagttgga atagtggtag cata                                          24

<210> SEQ ID NO 6
<211> LENGTH: 8
<212> TYPE: PRT
<213> ORGANISM: Artificial Sequence
<220> FEATURE:
<223> OTHER INFORMATION: Synthetic

<400> SEQUENCE: 6

Ile Ser Trp Asn Ser Gly Ser Ile
1               5

<210> SEQ ID NO 7
<211> LENGTH: 57
<212> TYPE: DNA
<213> ORGANISM: Artificial Sequence
<220> FEATURE:
<223> OTHER INFORMATION: Synthetic

<400> SEQUENCE: 7
gcaaaagatg gaggcagcag ctggttaccg ttcgtctact actacggtat ggacgtc     57

<210> SEQ ID NO 8
<211> LENGTH: 19
<212> TYPE: PRT
<213> ORGANISM: Artificial Sequence
<220> FEATURE:
<223> OTHER INFORMATION: Synthetic

<400> SEQUENCE: 8

Ala Lys Asp Gly Gly Ser Ser Trp Leu Pro Phe Val Tyr Tyr Tyr Gly
1               5                   10                  15

Met Asp Val

<210> SEQ ID NO 9
<211> LENGTH: 325
<212> TYPE: DNA
<213> ORGANISM: Artificial Sequence
<220> FEATURE:
<223> OTHER INFORMATION: Synthetic

<400> SEQUENCE: 9
gaaatagtga tgacgcagtc tccagccacc ctgtctgtgt ctcccgggga aagagccacc     60
ctctcctgca gggccagtca gagtattagc agcaactttg cctggtacca gcagaaacct    120
ggccaggctc ccaggctcct catctatggt gcatccacca gggccactgg tatcccagcc    180
aggttcagtg gcagtgggtc tgggacagac ttcactctca ccatcagcag cctgcagtct    240
gaagattttg cagtttatta ctgtcagcag tatagtagct ggcctccgta cacttttggc    300
cagggaccaa gctggagat caaac                                           325

<210> SEQ ID NO 10
<211> LENGTH: 108
<212> TYPE: PRT
<213> ORGANISM: Artificial Sequence

```
<220> FEATURE:
<223> OTHER INFORMATION: Synthetic

<400> SEQUENCE: 10

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Ser Asn
            20                  25                  30

Phe Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Val Tyr Tyr Cys Gln Gln Tyr Ser Ser Trp Pro Pro
                85                  90                  95

Tyr Thr Phe Gly Gln Gly Thr Lys Leu Glu Ile Lys
            100                 105

<210> SEQ ID NO 11
<211> LENGTH: 18
<212> TYPE: DNA
<213> ORGANISM: Artificial Sequence
<220> FEATURE:
<223> OTHER INFORMATION: Synthetic

<400> SEQUENCE: 11
cagagtatta gcagcaac                                                       18

<210> SEQ ID NO 12
<211> LENGTH: 6
<212> TYPE: PRT
<213> ORGANISM: Artificial Sequence
<220> FEATURE:
<223> OTHER INFORMATION: Synthetic

<400> SEQUENCE: 12

Gln Ser Ile Ser Ser Asn
1               5

<210> SEQ ID NO 13
<211> LENGTH: 9
<212> TYPE: DNA
<213> ORGANISM: Artificial Sequence
<220> FEATURE:
<223> OTHER INFORMATION: Synthetic

<400> SEQUENCE: 13 ggtgcatcc                                                                  9

<210> SEQ ID NO 14
<211> LENGTH: 3
<212> TYPE: PRT
<213> ORGANISM: Artificial Sequence
<220> FEATURE:
<223> OTHER INFORMATION: Synthetic

<400> SEQUENCE: 14

Gly Ala Ser
1
```

<210> SEQ ID NO 15
<211> LENGTH: 30
<212> TYPE: DNA
<213> ORGANISM: Artificial Sequence
<220> FEATURE:
<223> OTHER INFORMATION: Synthetic

<400> SEQUENCE: 15
cagcagtata gtagctggcc tccgtacact          30

<210> SEQ ID NO 16
<211> LENGTH: 10
<212> TYPE: PRT
<213> ORGANISM: Artificial Sequence
<220> FEATURE:
<223> OTHER INFORMATION: Synthetic

<400> SEQUENCE: 16

Gln Gln Tyr Ser Ser Trp Pro Pro Tyr Thr
 1               5                  10

<210> SEQ ID NO 17
<211> LENGTH: 349
<212> TYPE: DNA
<213> ORGANISM: Artificial Sequence
<220> FEATURE:
<223> OTHER INFORMATION: Synthetic

<400> SEQUENCE: 17
gaagtgcagc tggtggagtc tgggggaggc ttggttcagc ctggcaggtc cctgagactc      60
tcctgtgcag cctctagatt tacctttgat gattatgcca tgcactgggt ccggcaagct     120
ccagggaagg gcctggagtg ggtctcaggt attagttgga atagtggtag aataggttat     180
gcggactctg tgaagggccg attcaccatc tccagagaca cgccgagaa ctccctcttt     240
ctgcaaatga acggtctgag agcagaggac acggccttgt attactgtgc aaaaggccga     300
gattcttttg atatctgggg ccaagggaca atggtcaccg tctcttcag               349

<210> SEQ ID NO 18
<211> LENGTH: 116
<212> TYPE: PRT
<213> ORGANISM: Artificial Sequence
<220> FEATURE:
<223> OTHER INFORMATION: Synthetic

<400> SEQUENCE: 18

Glu Val Gln Leu Val Glu Ser Gly Gly Gly Leu Val Gln Pro Gly Arg
 1               5                  10                  15

Ser Leu Arg Leu Ser Cys Ala Ala Ser Arg Phe Thr Phe Asp Asp Tyr
             20                  25                  30

Ala Met His Trp Val Arg Gln Ala Pro Gly Lys Gly Leu Glu Trp Val
         35                  40                  45

Ser Gly Ile Ser Trp Asn Ser Gly Arg Ile Gly Tyr Ala Asp Ser Val
     50                  55                  60

Lys Gly Arg Phe Thr Ile Ser Arg Asp Asn Ala Glu Asn Ser Leu Phe
 65                  70                  75                  80

Leu Gln Met Asn Gly Leu Arg Ala Glu Asp Thr Ala Leu Tyr Tyr Cys
                 85                  90                  95

Ala Lys Gly Arg Asp Ser Phe Asp Ile Trp Gly Gln Gly Thr Met Val
            100                 105                 110

Thr Val Ser Ser
        115

<210> SEQ ID NO 19
<211> LENGTH: 24
<212> TYPE: DNA
<213> ORGANISM: Artificial Sequence
<220> FEATURE:
<223> OTHER INFORMATION: Synthetic

<400> SEQUENCE: 19
agatttacct ttgatgatta tgcc                                              24

<210> SEQ ID NO 20
<211> LENGTH: 8
<212> TYPE: PRT
<213> ORGANISM: Artificial Sequence
<220> FEATURE:
<223> OTHER INFORMATION: Synthetic

<400> SEQUENCE: 20

Arg Phe Thr Phe Asp Asp Tyr Ala
1               5

<210> SEQ ID NO 21
<211> LENGTH: 24
<212> TYPE: DNA
<213> ORGANISM: Artificial Sequence
<220> FEATURE:
<223> OTHER INFORMATION: Synthetic

<400> SEQUENCE: 21
attagttgga atagtggtag aata                                              24

<210> SEQ ID NO 22
<211> LENGTH: 8
<212> TYPE: PRT
<213> ORGANISM: Artificial Sequence
<220> FEATURE:
<223> OTHER INFORMATION: Synthetic

<400> SEQUENCE: 22

Ile Ser Trp Asn Ser Gly Arg Ile
1               5

<210> SEQ ID NO 23
<211> LENGTH: 27
<212> TYPE: DNA
<213> ORGANISM: Artificial Sequence
<220> FEATURE:
<223> OTHER INFORMATION: Synthetic

<400> SEQUENCE: 23
gcaaaaggcc gagattcttt tgatatc                                           27

<210> SEQ ID NO 24
<211> LENGTH: 9
<212> TYPE: PRT
<213> ORGANISM: Artificial Sequence
<220> FEATURE:
<223> OTHER INFORMATION: Synthetic

<400> SEQUENCE: 24

Ala Lys Gly Arg Asp Ser Phe Asp Ile
1               5

<210> SEQ ID NO 25
<211> LENGTH: 322
<212> TYPE: DNA
<213> ORGANISM: Artificial Sequence
<220> FEATURE:
<223> OTHER INFORMATION: Synthetic

<400> SEQUENCE: 25

```
gacatccaga tgacccagtc tccatcttcc gtgtctgcat ctgtaggaga cagagtcacc    60
atcacttgtc gggcgagtca gggtattagc agctggttag cctggtatca gcagaaacca   120
gggaaagccc ctaagctcct gatctatggt gcatccagtt tggaaagtgg ggtcccatca   180
aggttcagcg gcagtggatc tgggacagat ttcactctca ccatcagcag cctgcagcct   240
gaagattttg caagttatta ttgtcaacag gctaacagtt cccgtacac ttttggccag    300
gggaccaagc tggagatcaa ac                                             322
```

<210> SEQ ID NO 26
<211> LENGTH: 107
<212> TYPE: PRT
<213> ORGANISM: Artificial Sequence
<220> FEATURE:
<223> OTHER INFORMATION: Synthetic

<400> SEQUENCE: 26

```
Asp Ile Gln Met Thr Gln Ser Pro Ser Ser Val Ser Ala Ser Val Gly
1               5                   10                  15
Asp Arg Val Thr Ile Thr Cys Arg Ala Ser Gln Gly Ile Ser Ser Trp
            20                  25                  30
Leu Ala Trp Tyr Gln Gln Lys Pro Gly Lys Ala Pro Lys Leu Leu Ile
        35                  40                  45
Tyr Gly Ala Ser Ser Leu Glu Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Ser Tyr Tyr Cys Gln Gln Ala Asn Ser Phe Pro Tyr
                85                  90                  95
Thr Phe Gly Gln Gly Thr Lys Leu Glu Ile Lys
            100                 105
```

<210> SEQ ID NO 27
<211> LENGTH: 18
<212> TYPE: DNA
<213> ORGANISM: Artificial Sequence
<220> FEATURE:
<223> OTHER INFORMATION: Synthetic

<400> SEQUENCE: 27

```
cagggtatta gcagctgg                                                   18
```

<210> SEQ ID NO 28
<211> LENGTH: 6
<212> TYPE: PRT
<213> ORGANISM: Artificial Sequence
<220> FEATURE:
<223> OTHER INFORMATION: Synthetic

<400> SEQUENCE: 28

```
Gln Gly Ile Ser Ser Trp
1               5
```

<210> SEQ ID NO 29
<211> LENGTH: 9
<212> TYPE: DNA
<213> ORGANISM: Artificial Sequence
<220> FEATURE:
<223> OTHER INFORMATION: Synthetic

<400> SEQUENCE: 29 ggtgcatcc                                                                                           9

<210> SEQ ID NO 30
<211> LENGTH: 3
<212> TYPE: PRT
<213> ORGANISM: Artificial Sequence
<220> FEATURE:
<223> OTHER INFORMATION: Synthetic

<400> SEQUENCE: 30

Gly Ala Ser
1

<210> SEQ ID NO 31
<211> LENGTH: 27
<212> TYPE: DNA
<213> ORGANISM: Artificial Sequence
<220> FEATURE:
<223> OTHER INFORMATION: Synthetic

<400> SEQUENCE: 31
caacaggcta acagtttccc gtacact                                                                      27

<210> SEQ ID NO 32
<211> LENGTH: 9
<212> TYPE: PRT
<213> ORGANISM: Artificial Sequence
<220> FEATURE:
<223> OTHER INFORMATION: Synthetic

<400> SEQUENCE: 32

Gln Gln Ala Asn Ser Phe Pro Tyr Thr
1               5

<210> SEQ ID NO 33
<211> LENGTH: 349
<212> TYPE: DNA
<213> ORGANISM: Artificial Sequence
<220> FEATURE:
<223> OTHER INFORMATION: Synthetic

<400> SEQUENCE: 33
gaagtgcagc tggtggagtc tgggggaggc ttggtacagc ctggcaggtc cctgagactc        60
tcctgtgcag cctctggatt cacctttgat gattatgccc tgcactgggt ccggcaagct       120
ccagggaagg gcctggagtg gtctcaggt gttagttgga atggtggtag ataggctat         180 gcggactctg tgaaaggccg attcaccatc tccagagaca cgccaagaa ctccctcttt        240 ctgcaaatga acagtctgag agttgaggac acggccttgt attattgtgc aaaaggccgg       300
gatgcttttg atatctgggg ccaagggaca ttggtcaccg tctcttcag                   349

<210> SEQ ID NO 34
<211> LENGTH: 116
<212> TYPE: PRT
<213> ORGANISM: Artificial Sequence
<220> FEATURE:
<223> OTHER INFORMATION: Synthetic

<400> SEQUENCE: 34

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Leu His Trp Val Arg Gln Ala Pro Gly Lys Gly Leu Glu Trp Val
        35                  40                  45

Ser Gly Val Ser Trp Asn Gly Gly Arg Ile Gly Tyr Ala Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Val Glu Asp Thr Ala Leu Tyr Tyr Cys
                85                  90                  95

Ala Lys Gly Arg Asp Ala Phe Asp Ile Trp Gly Gln Gly Thr Leu Val
            100                 105                 110

Thr Val Ser Ser
        115

<210> SEQ ID NO 35
<211> LENGTH: 24
<212> TYPE: DNA
<213> ORGANISM: Artificial Sequence
<220> FEATURE:
<223> OTHER INFORMATION: Synthetic

<400> SEQUENCE: 35
ggattcacct ttgatgatta tgcc                                          24

<210> SEQ ID NO 36
<211> LENGTH: 8
<212> TYPE: PRT
<213> ORGANISM: Artificial Sequence
<220> FEATURE:
<223> OTHER INFORMATION: Synthetic

<400> SEQUENCE: 36

Gly Phe Thr Phe Asp Asp Tyr Ala
1               5

<210> SEQ ID NO 37
<211> LENGTH: 24
<212> TYPE: DNA
<213> ORGANISM: Artificial Sequence
<220> FEATURE:
<223> OTHER INFORMATION: Synthetic

<400> SEQUENCE: 37
gttagttgga atggtggtag aata                                          24

<210> SEQ ID NO 38
<211> LENGTH: 8
<212> TYPE: PRT
<213> ORGANISM: Artificial Sequence
<220> FEATURE:
<223> OTHER INFORMATION: Synthetic

<400> SEQUENCE: 38

Val Ser Trp Asn Gly Gly Arg Ile
1               5

<210> SEQ ID NO 39
<211> LENGTH: 27
<212> TYPE: DNA
<213> ORGANISM: Artificial Sequence
<220> FEATURE:
<223> OTHER INFORMATION: Synthetic

<400> SEQUENCE: 39
gcaaaaggcc gggatgcttt tgatatc                                              27

<210> SEQ ID NO 40
<211> LENGTH: 9
<212> TYPE: PRT
<213> ORGANISM: Artificial Sequence
<220> FEATURE:
<223> OTHER INFORMATION: Synthetic

<400> SEQUENCE: 40

Ala Lys Gly Arg Asp Ala Phe Asp Ile
1               5

<210> SEQ ID NO 41
<211> LENGTH: 322
<212> TYPE: DNA
<213> ORGANISM: Artificial Sequence
<220> FEATURE:
<223> OTHER INFORMATION: Synthetic

<400> SEQUENCE: 41
gacatccaga tgacccagtc tccatcttcc gtgtctgcat ctgtaggaga cagagtcacc          60
atcacttgtc gggcgagtca gggtattagc agctggttag cctggtatca gcagaaacca         120
gggaaagccc ctaaactcct gatctatgct gcatccagtt tgcaaagtgg ggtcccatca         180
aggttcagcg gcagtggatc tgggacagat tcactctcac ccatcagcag cctgcagcct         240
gaagattttg caacttacta ttgtcaacat gcttacagtt cccgtacac ttttggccag          300 gggaccaagc tggagatcaa ac                                                  322

<210> SEQ ID NO 42
<211> LENGTH: 107
<212> TYPE: PRT
<213> ORGANISM: Artificial Sequence
<220> FEATURE:
<223> OTHER INFORMATION: Synthetic

<400> SEQUENCE: 42

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Ala Tyr Ser Phe Pro Tyr
                85                  90                  95

Thr Phe Gly Gln Gly Thr Lys Leu Glu Ile Lys
            100                 105

```
<210> SEQ ID NO 43
<211> LENGTH: 18
<212> TYPE: DNA
<213> ORGANISM: Artificial Sequence
<220> FEATURE:
<223> OTHER INFORMATION: Synthetic

<400> SEQUENCE: 43
cagggtatta gcagctgg                                                 18

<210> SEQ ID NO 44
<211> LENGTH: 6
<212> TYPE: PRT
<213> ORGANISM: Artificial Sequence
<220> FEATURE:
<223> OTHER INFORMATION: Synthetic

<400> SEQUENCE: 44

Gln Gly Ile Ser Ser Trp
1               5

<210> SEQ ID NO 45
<211> LENGTH: 9
<212> TYPE: DNA
<213> ORGANISM: Artificial Sequence
<220> FEATURE:
<223> OTHER INFORMATION: Synthetic

<400> SEQUENCE: 45 gctgcatcc                                                            9

<210> SEQ ID NO 46
<211> LENGTH: 3
<212> TYPE: PRT
<213> ORGANISM: Artificial Sequence
<220> FEATURE:
<223> OTHER INFORMATION: Synthetic

<400> SEQUENCE: 46

Ala Ala Ser
1

<210> SEQ ID NO 47
<211> LENGTH: 27
<212> TYPE: DNA
<213> ORGANISM: Artificial Sequence
<220> FEATURE:
<223> OTHER INFORMATION: Synthetic

<400> SEQUENCE: 47
caacatgctt acagtttccc gtacact                                       27

<210> SEQ ID NO 48
<211> LENGTH: 9
<212> TYPE: PRT
<213> ORGANISM: Artificial Sequence
<220> FEATURE:
<223> OTHER INFORMATION: Synthetic

<400> SEQUENCE: 48

Gln His Ala Tyr Ser Phe Pro Tyr Thr
1               5

<210> SEQ ID NO 49
<211> LENGTH: 361
<212> TYPE: DNA
<213> ORGANISM: Artificial Sequence
```

<220> FEATURE:
<223> OTHER INFORMATION: Synthetic

<400> SEQUENCE: 49

```
caggtgcagc tggtgcagtc tggggctgag gtgaaagagc ctggggcctc agtgaaggtc    60
tcctgcaagg cttctggata caccttcacc tcttatgata tcatctgggt gcgacaggcc   120
actggacaag gcttgagtg atgggatgg atgaacccaa acagtggtaa cacaggctat    180
acacagaacc tccagggcag agtcaccttg accaggaaca cctccataac tacagtctac   240
atggaactga gcagcctgag ctctgaggac acggccgttt attactgtgc gcgagactac   300
agtagccact actacggttt ggacgtctgg ggccaaggga ccacggtcac cgtctcctca   360
a                                                                   361
```

<210> SEQ ID NO 50
<211> LENGTH: 120
<212> TYPE: PRT
<213> ORGANISM: Artificial Sequence
<220> FEATURE:
<223> OTHER INFORMATION: Synthetic

<400> SEQUENCE: 50

```
Gln Val Gln Leu Val Gln Ser Gly Ala Glu Val Lys Glu Pro Gly Ala
1               5                   10                  15
Ser Val Lys Val Ser Cys Lys Ala Ser Gly Tyr Thr Phe Thr Ser Tyr
            20                  25                  30
Asp Ile Ile Trp Val Arg Gln Ala Thr Gly Gln Gly Leu Glu Trp Met
        35                  40                  45
Gly Trp Met Asn Pro Asn Ser Gly Asn Thr Gly Tyr Thr Gln Asn Leu
    50                  55                  60
Gln Gly Arg Val Thr Leu Thr Arg Asn Thr Ser Ile Thr Thr Val Tyr
65                  70                  75                  80
Met Glu Leu Ser Ser Leu Ser Ser Glu Asp Thr Ala Val Tyr Tyr Cys
                85                  90                  95
Ala Arg Asp Tyr Ser Ser His Tyr Tyr Gly Leu Asp Val Trp Gly Gln
            100                 105                 110
Gly Thr Thr Val Thr Val Ser Ser
        115                 120
```

<210> SEQ ID NO 51
<211> LENGTH: 24
<212> TYPE: DNA
<213> ORGANISM: Artificial Sequence
<220> FEATURE:
<223> OTHER INFORMATION: Synthetic

<400> SEQUENCE: 51

```
ggatacacct tcacctctta tgat                                           24
```

<210> SEQ ID NO 52
<211> LENGTH: 8
<212> TYPE: PRT
<213> ORGANISM: Artificial Sequence
<220> FEATURE:
<223> OTHER INFORMATION: Synthetic

<400> SEQUENCE: 52

```
Gly Tyr Thr Phe Thr Ser Tyr Asp
1               5
```

<210> SEQ ID NO 53
<211> LENGTH: 24
<212> TYPE: DNA
<213> ORGANISM: Artificial Sequence
<220> FEATURE:
<223> OTHER INFORMATION: Synthetic

<400> SEQUENCE: 53
atgaacccaa acagtggtaa caca                                          24

<210> SEQ ID NO 54
<211> LENGTH: 8
<212> TYPE: PRT
<213> ORGANISM: Artificial Sequence
<220> FEATURE:
<223> OTHER INFORMATION: Synthetic

<400> SEQUENCE: 54

Met Asn Pro Asn Ser Gly Asn Thr
1               5

<210> SEQ ID NO 55
<211> LENGTH: 39
<212> TYPE: DNA
<213> ORGANISM: Artificial Sequence
<220> FEATURE:
<223> OTHER INFORMATION: Synthetic

<400> SEQUENCE: 55
gcgcgagact acagtagcca ctactacggt ttggacgtc                          39

<210> SEQ ID NO 56
<211> LENGTH: 13
<212> TYPE: PRT
<213> ORGANISM: Artificial Sequence
<220> FEATURE:
<223> OTHER INFORMATION: Synthetic

<400> SEQUENCE: 56

Ala Arg Asp Tyr Ser Ser His Tyr Tyr Gly Leu Asp Val
1               5                   10

<210> SEQ ID NO 57
<211> LENGTH: 322
<212> TYPE: DNA
<213> ORGANISM: Artificial Sequence
<220> FEATURE:
<223> OTHER INFORMATION: Synthetic

<400> SEQUENCE: 57
gacatccagt tgacccagtc tccatccttc ctgtctacat ctataggaga cagagtcacc    60
atcacttgct gggccagtca ggacattagc aattatttag cctggtatca gcaaaaacca   120
gggaaagccc ctaagctcct gatctttgtt gcatccactt tgcagagtgg ggtcccatca   180
aggttcagcg gcagtggatc tgggacagaa ttcactctca caatcagtag cctgcagcct   240
gaggattttg caacttatta ctgtcaacag tttaatagtt acccgctcac tttcggcgga   300
gggaccaagg tggaaatcaa ac                                           322

<210> SEQ ID NO 58
<211> LENGTH: 107
<212> TYPE: PRT
<213> ORGANISM: Artificial Sequence
<220> FEATURE:
<223> OTHER INFORMATION: Synthetic

<400> SEQUENCE: 58

Asp Ile Gln Leu Thr Gln Ser Pro Ser Phe Leu Ser Thr Ser Ile Gly
1               5                   10                  15

Asp Arg Val Thr Ile Thr Cys Trp Ala Ser Gln Asp Ile Ser Asn Tyr
            20                  25                  30

Leu Ala Trp Tyr Gln Gln Lys Pro Gly Lys Ala Pro Lys Leu Leu Ile
        35                  40                  45

Phe Val Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
            100                 105

<210> SEQ ID NO 59
<211> LENGTH: 18
<212> TYPE: DNA
<213> ORGANISM: Artificial Sequence
<220> FEATURE:
<223> OTHER INFORMATION: Synthetic

<400> SEQUENCE: 59
caggacatta gcaattat                                               18

<210> SEQ ID NO 60
<211> LENGTH: 6
<212> TYPE: PRT
<213> ORGANISM: Artificial Sequence
<220> FEATURE:
<223> OTHER INFORMATION: Synthetic

<400> SEQUENCE: 60

Gln Asp Ile Ser Asn Tyr
1               5

<210> SEQ ID NO 61
<211> LENGTH: 9
<212> TYPE: DNA
<213> ORGANISM: Artificial Sequence
<220> FEATURE:
<223> OTHER INFORMATION: Synthetic

<400> SEQUENCE: 61 gttgcatcc                                                          9

<210> SEQ ID NO 62
<211> LENGTH: 3
<212> TYPE: PRT
<213> ORGANISM: Artificial Sequence
<220> FEATURE:
<223> OTHER INFORMATION: Synthetic

<400> SEQUENCE: 62

Val Ala Ser
1

<210> SEQ ID NO 63
<211> LENGTH: 30
<212> TYPE: DNA
<213> ORGANISM: Artificial Sequence

```
<220> FEATURE:
<223> OTHER INFORMATION: Synthetic

<400> SEQUENCE: 63
caacagttta atagttaccc gctcactttc                                              30

<210> SEQ ID NO 64
<211> LENGTH: 10
<212> TYPE: PRT
<213> ORGANISM: Artificial Sequence
<220> FEATURE:
<223> OTHER INFORMATION: Synthetic

<400> SEQUENCE: 64

Gln Gln Phe Asn Ser Tyr Pro Leu Thr Phe
1               5                   10

<210> SEQ ID NO 65
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Gly or Arg
<220> FEATURE:
<221> NAME/KEY: VARIANT
<222> LOCATION: (2)...(2)
<223> OTHER INFORMATION: Xaa = Phe or Tyr
<220> FEATURE:
<221> NAME/KEY: VARIANT
<222> LOCATION: (3)...(3)
<223> OTHER INFORMATION: Xaa = Ile or Thr
<220> FEATURE:
<221> NAME/KEY: VARIANT
<222> LOCATION: (4)...(4)
<223> OTHER INFORMATION: Xaa = Phe
<220> FEATURE:
<221> NAME/KEY: VARIANT
<222> LOCATION: (5)...(5)
<223> OTHER INFORMATION: Xaa = Asp or Thr
<220> FEATURE:
<221> NAME/KEY: VARIANT
<222> LOCATION: (6)...(6)
<223> OTHER INFORMATION: Xaa = Asp or Ser
<220> FEATURE:
<221> NAME/KEY: VARIANT
<222> LOCATION: (7)...(7)
<223> OTHER INFORMATION: Xaa = Tyr
<220> FEATURE:
<221> NAME/KEY: VARIANT
<222> LOCATION: (8)...(8)
<223> OTHER INFORMATION: Xaa = Ala or Asp

<400> SEQUENCE: 65

Xaa Xaa Xaa Xaa Xaa Xaa Xaa Xaa
1               5

<210> SEQ ID NO 66
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Ile, Val or Met
```

```
<220> FEATURE:
<221> NAME/KEY: VARIANT
<222> LOCATION: (2)...(2)
<223> OTHER INFORMATION: Xaa = Ser or Asn
<220> FEATURE:
<221> NAME/KEY: VARIANT
<222> LOCATION: (3)...(3)
<223> OTHER INFORMATION: Xaa = Thr or Pro
<220> FEATURE:
<221> NAME/KEY: VARIANT
<222> LOCATION: (4)...(4)
<223> OTHER INFORMATION: Xaa = Asn
<220> FEATURE:
<221> NAME/KEY: VARIANT
<222> LOCATION: (5)...(5)
<223> OTHER INFORMATION: Xaa = Ser or Gly
<220> FEATURE:
<221> NAME/KEY: VARIANT
<222> LOCATION: (6)...(6)
<223> OTHER INFORMATION: Xaa = Gly
<220> FEATURE:
<221> NAME/KEY: VARIANT
<222> LOCATION: (7)...(7)
<223> OTHER INFORMATION: Xaa = Ser, Arg or Asn
<220> FEATURE:
<221> NAME/KEY: VARIANT
<222> LOCATION: (8)...(8)
<223> OTHER INFORMATION: Xaa = Ile or Thr

<400> SEQUENCE: 66

Xaa Xaa Xaa Xaa Xaa Xaa Xaa Xaa
1               5

<210> SEQ ID NO 67
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Ala
<220> FEATURE:
<221> NAME/KEY: VARIANT
<222> LOCATION: (2)...(2)
<223> OTHER INFORMATION: Xaa = Lys or Arg
<220> FEATURE:
<221> NAME/KEY: VARIANT
<222> LOCATION: (3)...(3)
<223> OTHER INFORMATION: Xaa = Asp or Gly
<220> FEATURE:
<221> NAME/KEY: VARIANT
<222> LOCATION: (4)...(4)
<223> OTHER INFORMATION: Xaa = Gly, Arg or Tyr
<220> FEATURE:
<221> NAME/KEY: VARIANT
<222> LOCATION: (5)...(5)
<223> OTHER INFORMATION: Xaa = Gly, Asp or Ser
<220> FEATURE:
<221> NAME/KEY: VARIANT
<222> LOCATION: (6)...(6)
<223> OTHER INFORMATION: Xaa = Ser or Ala
<220> FEATURE:
<221> NAME/KEY: VARIANT
<222> LOCATION: (7)...(7)
<223> OTHER INFORMATION: Xaa = Ser, Phe or His
<220> FEATURE:
<221> NAME/KEY: VARIANT
<222> LOCATION: (8)...(8)
<223> OTHER INFORMATION: Xaa = Trp, Asp or Tyr
<220> FEATURE:
<221> NAME/KEY: VARIANT
<222> LOCATION: (9)...(9)
<223> OTHER INFORMATION: Xaa = Leu, Ile or Tyr
```

```
<220> FEATURE:
<221> NAME/KEY: VARIANT
<222> LOCATION: (10)...(10)
<223> OTHER INFORMATION: Xaa = Pro, Gly or absent
<220> FEATURE:
<221> NAME/KEY: VARIANT
<222> LOCATION: (11)...(11)
<223> OTHER INFORMATION: Xaa = Phe, Leu or absent
<220> FEATURE:
<221> NAME/KEY: VARIANT
<222> LOCATION: (12)...(12)
<223> OTHER INFORMATION: Xaa = Val, Asp or absent
<220> FEATURE:
<221> NAME/KEY: VARIANT
<222> LOCATION: (13)...(13)
<223> OTHER INFORMATION: Xaa = Tyr, Val or absent
<220> FEATURE:
<221> NAME/KEY: VARIANT
<222> LOCATION: (14)...(14)
<223> OTHER INFORMATION: Xaa = Tyr or absent
<220> FEATURE:
<221> NAME/KEY: VARIANT
<222> LOCATION: (15)...(15)
<223> OTHER INFORMATION: Xaa = Tyr or absent
<220> FEATURE:
<221> NAME/KEY: VARIANT
<222> LOCATION: (16)...(16)
<223> OTHER INFORMATION: Xaa = Gly or absent
<220> FEATURE:
<221> NAME/KEY: VARIANT
<222> LOCATION: (17)...(17)
<223> OTHER INFORMATION: Xaa = Met or absent
<220> FEATURE:
<221> NAME/KEY: VARIANT
<222> LOCATION: (18)...(18)
<223> OTHER INFORMATION: Xaa = Asp or absent
<220> FEATURE:
<221> NAME/KEY: VARIANT
<222> LOCATION: (19)...(19)
<223> OTHER INFORMATION: Xaa = Val or absent

<400> SEQUENCE: 67

Xaa Xaa Xaa Xaa Xaa Xaa Xaa Xaa Xaa Xaa Xaa Xaa Xaa Xaa Xaa Xaa
1               5                   10                  15

Xaa Xaa Xaa

<210> SEQ ID NO 68
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Gln
<220> FEATURE:
<221> NAME/KEY: VARIANT
<222> LOCATION: (2)...(2)
<223> OTHER INFORMATION: Xaa = Ser, Gly or Asp
<220> FEATURE:
<221> NAME/KEY: VARIANT
<222> LOCATION: (3)...(3)
<223> OTHER INFORMATION: Xaa = Ile
<220> FEATURE:
<221> NAME/KEY: VARIANT
<222> LOCATION: (4)...(4)
<223> OTHER INFORMATION: Xaa = Ser
<220> FEATURE:
<221> NAME/KEY: VARIANT
<222> LOCATION: (5)...(5)
<223> OTHER INFORMATION: Xaa = Ser or Asn
<220> FEATURE:
<221> NAME/KEY: VARIANT
<222> LOCATION: (6)...(6)
<223> OTHER INFORMATION: Xaa = Asn, Trp or Tyr
```

```
<400> SEQUENCE: 68

Xaa Xaa Xaa Xaa Xaa Xaa
1               5

<210> SEQ ID NO 69
<211> LENGTH: 3
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Gly, Ala or Val
<220> FEATURE:
<221> NAME/KEY: VARIANT
<222> LOCATION: (2)...(2)
<223> OTHER INFORMATION: Xaa = Ala
<220> FEATURE:
<221> NAME/KEY: VARIANT
<222> LOCATION: (3)...(3)
<223> OTHER INFORMATION: Xaa = Ser

<400> SEQUENCE: 69

Xaa Xaa Xaa
1

<210> SEQ ID NO 70
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Gln
<220> FEATURE:
<221> NAME/KEY: VARIANT
<222> LOCATION: (2)...(2)
<223> OTHER INFORMATION: Xaa = Gln or His
<220> FEATURE:
<221> NAME/KEY: VARIANT
<222> LOCATION: (3)...(3)
<223> OTHER INFORMATION: Xaa = Tyr, Ala or Phe
<220> FEATURE:
<221> NAME/KEY: VARIANT
<222> LOCATION: (4)...(4)
<223> OTHER INFORMATION: Xaa = Ser, Asn or Tyr
<220> FEATURE:
<221> NAME/KEY: VARIANT
<222> LOCATION: (5)...(5)
<223> OTHER INFORMATION: Xaa = Ser
<220> FEATURE:
<221> NAME/KEY: VARIANT
<222> LOCATION: (6)...(6)
<223> OTHER INFORMATION: Xaa = Trp, Phe or Tyr
<220> FEATURE:
<221> NAME/KEY: VARIANT
<222> LOCATION: (7)...(7)
<223> OTHER INFORMATION: Xaa = Pro
<220> FEATURE:
<221> NAME/KEY: VARIANT
<222> LOCATION: (8)...(8)
<223> OTHER INFORMATION: Xaa = Pro, Tyr or Leu
<220> FEATURE:
<221> NAME/KEY: VARIANT
<222> LOCATION: (9)...(9)
<223> OTHER INFORMATION: Xaa = Tyr or Thr
<220> FEATURE:
<221> NAME/KEY: VARIANT
<222> LOCATION: (10)...(10)
<223> OTHER INFORMATION: Xaa = Thr or absent
```

```
<400> SEQUENCE: 70

Xaa Xaa Xaa Xaa Xaa Xaa Xaa Xaa Xaa
1               5                   10

<210> SEQ ID NO 71
<211> LENGTH: 330
<212> TYPE: PRT
<213> ORGANISM: Artificial Sequence
<220> FEATURE:
<223> OTHER INFORMATION: Synthetic

<400> SEQUENCE: 71
```

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

```
<210> SEQ ID NO 72
<211> LENGTH: 327
<212> TYPE: PRT
<213> ORGANISM: Artificial Sequence
<220> FEATURE:
<223> OTHER INFORMATION: Synthetic

<400> SEQUENCE: 72

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 73
<211> LENGTH: 327
<212> TYPE: PRT
<213> ORGANISM: Artificial Sequence
<220> FEATURE:
<223> OTHER INFORMATION: Synthetic
```

<400> SEQUENCE: 73

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 74
<211> LENGTH: 358
<212> TYPE: PRT
<213> ORGANISM: Homo sapiens

<400> SEQUENCE: 74

Met Val Ala Val Gly Cys Ala Leu Leu Ala Leu Leu Ala Ala Pro
1               5                   10                  15

Gly Ala Ala Leu Ala Pro Arg Arg Cys Pro Ala Gln Glu Val Ala Arg
            20                  25                  30

-continued

```
Gly Val Leu Thr Ser Leu Pro Gly Asp Ser Val Thr Leu Thr Cys Pro
            35                  40                  45

Gly Val Glu Pro Glu Asp Asn Ala Thr Val His Trp Val Leu Arg Lys
 50                  55                  60

Pro Ala Ala Gly Ser His Pro Ser Arg Trp Ala Gly Met Gly Arg Arg
 65                  70                  75                  80

Leu Leu Leu Arg Ser Val Gln Leu His Asp Ser Gly Asn Tyr Ser Cys
                 85                  90                  95

Tyr Arg Ala Gly Arg Pro Ala Gly Thr Val His Leu Leu Val Asp Val
            100                 105                 110

Pro Pro Glu Glu Pro Gln Leu Ser Cys Phe Arg Lys Ser Pro Leu Ser
            115                 120                 125

Asn Val Val Cys Glu Trp Gly Pro Arg Ser Thr Pro Ser Leu Thr Thr
130                 135                 140

Lys Ala Val Leu Leu Val Arg Lys Phe Gln Asn Ser Pro Ala Glu Asp
145                 150                 155                 160

Phe Gln Glu Pro Cys Gln Tyr Ser Gln Glu Ser Gln Lys Phe Ser Cys
                165                 170                 175

Gln Leu Ala Val Pro Glu Gly Asp Ser Ser Phe Tyr Ile Val Ser Met
            180                 185                 190

Cys Val Ala Ser Ser Val Gly Ser Lys Phe Ser Lys Thr Gln Thr Phe
            195                 200                 205

Gln Gly Cys Gly Ile Leu Gln Pro Asp Pro Pro Ala Asn Ile Thr Val
            210                 215                 220

Thr Ala Val Ala Arg Asn Pro Arg Trp Leu Ser Val Thr Trp Gln Asp
225                 230                 235                 240

Pro His Ser Trp Asn Ser Ser Phe Tyr Arg Leu Arg Phe Glu Leu Arg
                245                 250                 255

Tyr Arg Ala Glu Arg Ser Lys Thr Phe Thr Thr Trp Met Val Lys Asp
            260                 265                 270

Leu Gln His His Cys Val Ile His Asp Ala Trp Ser Gly Leu Arg His
            275                 280                 285

Val Val Gln Leu Arg Ala Gln Glu Glu Phe Gly Gln Gly Glu Trp Ser
290                 295                 300

Glu Trp Ser Pro Glu Ala Met Gly Thr Pro Trp Thr Glu Ser Arg Ser
305                 310                 315                 320

Pro Pro Ala Glu Asn Glu Val Ser Thr Pro Met Gln Ala Leu Thr Thr
                325                 330                 335

Asn Lys Asp Asp Asp Asn Ile Leu Phe Arg Asp Ser Ala Asn Ala Thr
            340                 345                 350

Ser Leu Pro Val Gln Asp
            355
```